US012624173B2

(12) United States Patent
Sintov

(10) Patent No.: US 12,624,173 B2
(45) Date of Patent: **\*May 12, 2026**

(54) BIODEGRADABLE POLYMERIC COMPOSITIONS, METHODS OF PREPARATION AND USES THEREOF

(71) Applicant: B.G. NEGEV TECHNOLOGIES AND APPLICATIONS LTD., AT BEN-GURION UNIVERSITY, Beer Sheva (IL)

(72) Inventor: Amnon Sintov, Omer (IL)

(73) Assignee: B.G. NEGEV TECHNOLOGIES AND APPLICATIONS LTD., AT BEN-GURION UNIVERSITY, Beer Sheva (IL)

( \* ) Notice: Subject to any disclaimer, the term of this patent is extended or adjusted under 35 U.S.C. 154(b) by 936 days.

This patent is subject to a terminal disclaimer.

(21) Appl. No.: 17/829,302

(22) Filed: May 31, 2022

(65) Prior Publication Data

US 2022/0339286 A1 Oct. 27, 2022

Related U.S. Application Data

(63) Continuation of application No. 17/781,318, filed as application No. PCT/IL2020/051248 on Dec. 3, 2020.

(60) Provisional application No. 62/943,824, filed on Dec. 5, 2019.

(51) Int. Cl.
*C08J 3/14* (2006.01)
*A61K 9/00* (2006.01)
*A61K 9/107* (2006.01)
*A61K 9/19* (2006.01)
*A61K 9/51* (2006.01)
*A61K 9/70* (2006.01)
*A61K 31/047* (2006.01)
*A61K 31/12* (2006.01)
*A61K 31/46* (2006.01)
*A61K 38/28* (2006.01)
*A61K 47/36* (2006.01)
*A61K 47/38* (2006.01)
*A61K 47/64* (2017.01)

(52) U.S. Cl.
CPC .............. *C08J 3/14* (2013.01); *A61K 9/0043* (2013.01); *A61K 9/1075* (2013.01); *A61K 9/19* (2013.01); *A61K 9/5123* (2013.01); *A61K 9/5161* (2013.01); *A61K 9/5192* (2013.01); *A61K 9/7007* (2013.01); *A61K 31/047* (2013.01); *A61K 31/12* (2013.01); *A61K 31/46* (2013.01); *A61K 38/28* (2013.01); *A61K 47/36* (2013.01); *A61K 47/38* (2013.01); *A61K 47/64* (2017.08); *C08J 2301/28* (2013.01); *C08J 2303/04* (2013.01); *C08J 2305/04* (2013.01)

(58) Field of Classification Search
None
See application file for complete search history.

(56) References Cited

U.S. PATENT DOCUMENTS

| | | | |
|---|---|---|---|
| 5,846,530 A | 12/1998 | Soon-Shiong et al. | |
| 6,313,105 B1 | 11/2001 | Bengs et al. | |
| 6,383,513 B1 | 5/2002 | Watts et al. | |
| 6,790,840 B1 | 9/2004 | Lee et al. | |
| 7,255,732 B2 | 8/2007 | Fischer et al. | |
| 2008/0102114 A1 | 5/2008 | Koritala et al. | |
| 2013/0158126 A1 | 6/2013 | Munoz Blanco et al. | |
| 2017/0240937 A1\* | 8/2017 | Grelier .................. C07C 67/343 | |
| 2018/0318230 A1\* | 11/2018 | Chopra .................. A61K 38/28 | |

FOREIGN PATENT DOCUMENTS

| | | | | |
|---|---|---|---|---|
| CN | 105884930 A | 8/2016 | | |
| JP | 2003238734 A | 8/2003 | | |
| WO | WO-2008096351 A1 \* | 8/2008 | ........... | A61K 31/335 |
| WO | 2015044293 A1 | 4/2015 | | |
| WO | WO-2021072012 A1 \* | 4/2021 | ......... | C08B 37/0096 |

OTHER PUBLICATIONS

Zhang et al. Synthesis of Multiresponsive and Dynamic Chitosan-Based Hydrogels for Controlled Release of Bioactive Molecules. Biomacromolecules. 2011 12 (8), 2894-2901. DOI: 10.1021/bm200423f (Year: 2011).\*
Li et al. Development of drug-loaded chitosan-vanillin nanoparticles and its cytotoxicity against HT-29 cells. Drug Deliv. 2016;23(1): 30-5. doi: 10.3109/10717544.2014.900590. Epub Apr. 9, 2014. (Year: 2014).\*
Bechgaard et al. Intranasal administration of insulin to rabbits using glycofurol as an absorption promoter, International Journal of Pharmaceutics, vol. 128, Issues 1-2, 1996, pp. 287-289, https://doi. org/10.1016/0378-5173(95)04315-2. (Year: 1996).\*

(Continued)

*Primary Examiner* — Daniel E Kolker
*Assistant Examiner* — Julia A Rossi
(74) *Attorney, Agent, or Firm* — Roach Brown McCarthy & Gruber, P.C.; Kevin D. McCarthy

(57) ABSTRACT

Disclosed herein compositions of polysaccharides chemically cross-linked by aromatic dialdehydes. The compositions may be in form of polymeric sheets for a variety of applications. Disclosed also nano-sized particles comprising the polysaccharide chemically cross-linked by aromatic dialdehydes. The nano-sized particles may further comprise lipids and surfactants. Intranasal delivery of the nano-sized particles enables delivery of biologically active agents into the brain. Topical and transdermal delivery of the nano-sized particles enables delivery of biologically active agents for treatment of systemic or dermatological disorders. Methods of manufacturing and uses of the compositions are also disclosed.

10 Claims, 10 Drawing Sheets

(56) References Cited

OTHER PUBLICATIONS

Rachmawati et al. The In Vitro-In Vivo Safety Confirmation of PEG-40 Hydrogenated Castor Oil as a Surfactant for Oral Nanoemulsion Formulation. Sci Pharm. Mar. 31, 2017;85(2):18. doi: 10.3390/scipharm85020018. (Year: 2017).*

International Search Report for PCT/IL2020/051248; mailed Feb. 21, 2021 (4 pages).

Written Opinion of the International Searching Authority for PCT/IL2020/051248; mailed Feb. 21, 2021 (7 pages).

Li et al.; "Development of drug-loaded chitosan-vanillin nanoparticales and its cytotoxicity against HT-29 cells"; Drug Deliv 2016;23(1):30-5. doi: 10.3109/10717544.2014.900590. Epub Apr. 9, 2014.—abstract only.

Tomadoni et al.; "Vanillin as a natural cross-linking agent in chitosan-based films: Optimizing formulation by response surface methodology;" Polymer Testing; 10.1016/j.polyertesting Sep. 2019. 105935. Sep. 30, 2019.

Chin et al, "Preparation and Characterization of Starch Nanoparticles for Controlled Release of Curcumin"; International Journal of Polymer Science, vol. 2014, Article ID 340121, 2014; 9 pages.

Wang et al.: "Effect of vapor-phase glutaraldehyde crosslinking on electrospun starch fibers", Carbohydrate Polymers, Applied Science Publishers, Ltd Barking, GB, vol. 140, Dec. 29, 2015 (Dec. 29, 2015), pp. 356-361, (6 pages).

Sintov: "AmyloLipid Nanovesicles: A self-assembled lipid-modified starch hybrid system constructed for direct nose-to-brain delivery of curcumin", International Journal of Pharmaceutics, Elsevier, NL, vol. 588, Aug. 5, 2020 (Aug. 5, 2020), XP086272356 (6 pages).

Kavianinia et al., "Preparation and characterization of chitosan films, crosslinked with symmetric aromatic dianhydrides to achieve enhanced thermal properties", Polymer international, vol. 64, Issue 4, p. 556-562; Nov. 7, 2014 (7 pages).

Thatte, M. R., Synthesis and antibacterial assessment of water-soluble hydrophobic chitosan derivatives bearing quaternary ammonium functionality, LSU Doctoral Dissertations, Louisiana State University, 2004, pp. 1-107 (122 pages).

Thyrlyalakshmi et al., Fabrication of chitosan-bis (4-formyl-2 methoxy phenyl carbonate) Schiff base nanoparticles and evaluation of their antioxidant and anticancer properties: Molecular Biology Reports, May 2019, vol. 46, pp. 4333-4347 (16 pages).

Kavianinia et al. Preparation and characterization of chitosan films, crosslinked with symmetric aromatic dianhydrides to acheive enhanced thermal properties; Polym Int 2015;64:556-562 (7 pages).

Hirano et al.: "Structural analysis of the reaction products of chitosan with o-, m- and p-phthalaldehydes", International Journal of Biological Macromolecules, Elsevier BV, NL, vol. 5, No. 6, Dec. 1, 1983 (Dec. 1, 1983), pp. 373-376, XP025215895 (4 pages).

Thyriyalakshmi et al., "Fabrication of chitosan-bis (4-formyl-2 methoxy phenyl carbonate) Schiff base nanoparticles and evaluation of their antioxidant and anticancer properties"; Molecular Biology Reports, (year 2019) 05, vol. 46, pp. 4333-4347 (16 pages).

Geng et al., "Vanillin-Based Polyschiff Vitrimers: Reprocessability and Chemical Recyclability"; ACS Sustainable Chem. Eng. 2018, 6, 15463-15470 (Year: 2018) (8 pages).

Hong et al., "Proline-mediated dimerization of cinnamaldehydes via 1.3-dipolar cycloaddition reaction with azomethine ylides. A rapid access to highly functionalized hexahydro-aH-ryrrolizine"; Tetrahedron Letters 49 (38) (year 2008) (Abstract) (5 pages).

Ito et al., "Coniferyl aldehyde dimers in dehydrogenative polymerization: model of abnormal lignin formation in cinnayle alcohol dehyrogenase-deficient plants"; J. Wood Sci (year 2002) 48: 216-221 (6 pages).

Haplot et al. "Oxidative Dimerization of Phenolic Aldehydes related to Lignin Formation", J. Phys Chem (year 1994) 98: 2641-2645 (first page).

Zhao et al., "An injectable particle-hydrogel hybrid systems for glucose-regulatory insulin delivery"; Acta Biomaterialia, vol. 64, pp. 334-345 (Year: 2017) (12 pages).

Navari et al., "Antiemetic Prophylaxis for Chemotherapy-Induced Nausea and Vomiting"; N Engl J Med, 2016, vol. 374, pp. 1356-1367) (Year: 2016) (12 pages).

Gaur et al., "Dehydrodivanillin: Multi-dimensional NMR Spectral Studies, Surface Morphology and Electrical Characteristics of Thin Films"; Bull. Korean Chem. Soc. 2009, vol. 30, pp. 2895-2898) (Year: 2009) (4 pages).

Saikia et al., "Effect of crosslinker on drug delivery properties of curcumin loaded starch coated iron oxide nanoparticles"; International Journal of Biological Macromolecules, 2016, vol. 93, pp. 1121-1132) (Year: 2016) (12 pages).

Chemical information and structure of Divanillin. Obtained from PubChem < URL: https://pubchem.ncbi.nlm.nih.gov/compound/95086 > on Aug. 14, 2025 (Year: 2025).

* cited by examiner

Radius [nm] (Unweighted log.)

FIGURE 11C

BIODEGRADABLE POLYMERIC COMPOSITIONS, METHODS OF PREPARATION AND USES THEREOF

BACKGROUND OF THE INVENTION

In the last two decades, the worldwide demand for environmentally friendly materials in most fields of day-to-day life was vastly increased due to a deeper understanding of the risks and the extensive damage to both human health and the disastrous environmental effects.

The use of biodegradable materials in the place of traditional petroleum-based plastic polymers has increased, and the efforts directed to find mechanically stable and robust alternatives are extensively studied. The most common biodegradable materials utilized today are polyhydroxyalkanoates, for example, polyhydroxy 3-butyrate (PHB), starch blends and cellulose based materials. Different combinations and chemical processes were developed over the years in order to promote the use of biodegradable materials and their incorporation into the industry, for example, as an alternative for nylon bags and packaging material for food products.

Biodegradable materials also found extensive use in biomedical devices, tissue engineering and other applications, e.g. sutures, surgical fixation devices and drug delivery. To date, polymeric materials are widely used in drug delivery systems, as they are biologically compatible, and their mechanical properties and their degradation rates can be often tuned and optimized according to the preferred use. For example, one commercially available material is polylactic acid (PLA). Lactic acid is commonly produced via fermentation of dextrose extracted from a starch source, therefore, requires several other processes prior to the synthesis of PLA from lactic acid monomers.

Another important characteristic and an advantageous feature of biodegradable polymers is the fact that they can serve as delivery systems for pharmaceuticals, e.g., by providing protection to a drug by preventing its exposure to physiological conditions, or by improving the solubility of a poorly-soluble or insoluble drug, and thus, at times, increase the drug's bioavailability. These abovementioned advantageous properties promote a safe and improved medical treatment and patient compliance, and therefore are sought after in the pharmaceutical industry.

In this regard, modified polysaccharides, e.g. starches and alginates, are an appealing option. For example, U.S. Pat. No. 5,846,530 discloses chemically cross-linkable alginates. A further U.S. Pat. No. 6,313,105 discloses a thermoplastic mixture of natural and "dialdehyde starch", i.e. starch oxidized to aldehyde groups. The U.S. Pat. No. 6,790,840 discloses reversibly crosslinked hydrogels, such as alginates. Also, the U.S. Pat. No. 7,255,732 compositions obtainable by thermomechanical gelatinization of starch with dialdehyde starch. Additionally, native starch was reported for the preparation of nanoparticles containing the active agent curcumin, in Suk Fin Chin et al, *International Journal of Polymer Science*, Volume 2014, Article ID 340121, with the digital object identified number doi: 10.1155/2014/340121.

Thus, there is a need in the art to provide a both time and resources efficient methodology, to obtain a biodegradable material having compatible proprieties to serve in the above-described systems.

SUMMARY OF THE INVENTION

Provided herein is a composition of matter comprising a polysaccharide chemically crosslinked by an aromatic dialdehyde. The aromatic dialdehyde may usually be selected from the group consisting of divanillin, di-cinnamaldehyde, di-coniferylaldehyde, di-coumaraldehyde, and di-sinapaldehyde. Preferably, the polysaccharide is a starch, an alginic acid, or hydroxypropyl cellulose. In currently preferred embodiments, the polysaccharide is a starch, and the aromatic dialdehyde is divanillin. The composition may be present in a form of a polymeric sheet, or a polymeric particle/capsule.

In a further aspect provided a pharmaceutically acceptable formulation comprising the composition of a polysaccharide chemically crosslinked by an aromatic dialdehyde. Preferably, the formulation is in form of nano-sized particles. The formulation usually comprises a bioactive material. The bioactive material may preferably be a naturally occurring substance, an antibiotic, or a CNS-active drug, e.g. curcumin or a cannabinoid, such as cannabidiol, an antiemetic, such as granisetron, or a peptide or polypeptide, such as insulin, or glycoprotein, oligonucleotide, antibody drug conjugate, or peptide drug conjugate.

The composition, particularly nano-sized particles, may further comprise a lipid and/or a surfactant and/or a cosolvent, e.g. those as may be used in the preparation of the nano-sized particles. Preferably, these lipid and/or a surfactant and/or a cosolvent are selected from the group consisting of caprylocaproyl polyoxyl-8 glyceride, polyoxyl-40 hydrogenated castor oil, propylene carbonate, tetraglycol, glyceryl oleate and dioleate, isopropyl palmitate, and cocoa butter.

In a further aspect provided herein a process of manufacturing of a polymeric composition. The process comprises combining in an aqueous medium a polysaccharide and an aromatic dialdehyde. Combining the polysaccharide with the aromatic dialdehyde may ultimately result in the polysaccharide being chemically cross-linked by the aromatic dialdehyde. The process may further comprise any one of the following steps: i) evaporating a solvent from a solution or an emulsion comprising said polysaccharide and said aromatic dialdehyde, ii) spray-drying a solution or an emulsion comprising said polysaccharide and said aromatic dialdehyde, iii) forming nano-sized particles comprising said polysaccharide and said aromatic dialdehyde by adding an anti-solvent, i.e. forming nano-particles by nanoprecipitation; iv) separating nano-sized particles comprising said polysaccharide and said aromatic dialdehyde by adding a salt, i.e. salting-out, or v) providing a microemulsion or a nanoemulsion comprising said polysaccharide and/or said aromatic dialdehyde. The aromatic dialdehyde may also be dispersed in the aqueous medium, and the medium may be either water, an aqueous buffer, acetic acid solution, or a hydro-organic solution. The aromatic dialdehyde may be selected as above, i.e. selected from the group consisting of divanillin, di-cinnamaldehyde, di-coniferylaldehyde, di-coumaraldehyde, and di-sinapaldehyde. Also, the polysaccharide may be as above, i.e. a starch, an alginic acid, or hydroxypropyl cellulose. The process may further comprise combining an acid or a base with the polysaccharide and/or the aromatic dialdehyde. The process may preferably further comprise combining the mixture with a bioactive material; the bioactive material is preferably substantially stable in presence of the aromatic dialdehyde. The bioactive material is preferably, as above, a naturally occurring substance, being optionally selected from the group consisting of curcumin, insulin, a cannabinoid e.g. cannabidiol, an antiemetic e.g. granisetron, and an antibiotic. In currently preferred embodiments, in the process the polysaccharide is a starch, the aromatic dialdehyde is divanillin, and the bioactive material is curcumin, granisetron, cannabidiol, or insulin.

The process may further comprise combing said polysaccharide and/or said aromatic dialdehyde with a lipid and a surfactant, and optionally a cosolvent, optionally in a form of a microemulsion. The process may also further comprise precipitating, optionally by solvent evaporation, and/or separating of a polymeric composition, in form of nanoparticles. Preferably, the lipid and/or a surfactant and/or a cosolvent are selected from the group consisting of caprylocaproyl polyoxyl-8 glyceride, polyoxyl-40 hydrogenated castor oil, propylene carbonate, tetraglycol, glyceryl oleate and dioleate, isopropyl palmitate, and cocoa butter. In currently preferred embodiments, the lipid comprises cocoa butter and a mixture of glyceryl oleate and dioleate, the surfactant comprises polyoxyl hydrogenated castor oil, and the cosolvent is tetraglycol.

In a further aspect provided herein a method of treatment of a subject in need thereof, the method comprising administering to said subject a composition as described herein, the composition comprising a therapeutically effective amount of the bioactive agent. Preferably, the bioactive agent is an agent having an activity in the central nervous system. In currently preferred embodiments, the administration is intranasal administration. Preferably, following the administration of the composition to a test non-human mammal a concentration in the brain of said test non-human mammal is at least 150 percent higher than the concentration in the brain obtained following an intravenous or subcutaneous administration to a reference test non-human mammal. The administration may also be a transdermal administration, an oral administration, a sublingual administration, an intrauterine administration, an implanting devices, or a parenteral administration.

Figure 1A:
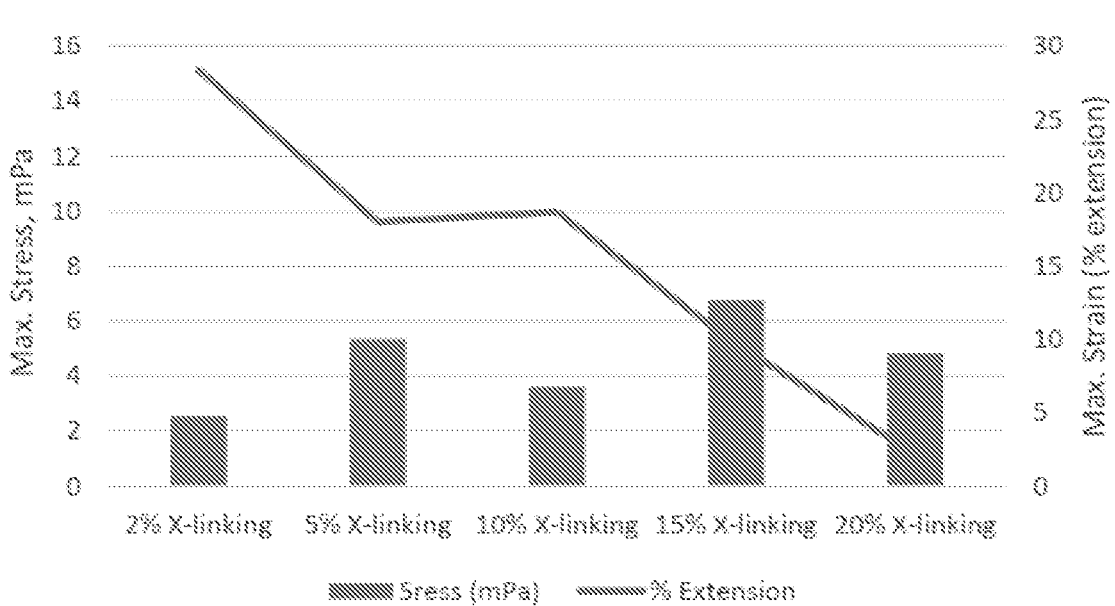
FIGS. 1a and 1b show the effect of divanillin levels on tensile strength and elongation of 200 micron-thick starch films without curing, as bar graph and as stress-strain curve, respectively.
Figure 1B:
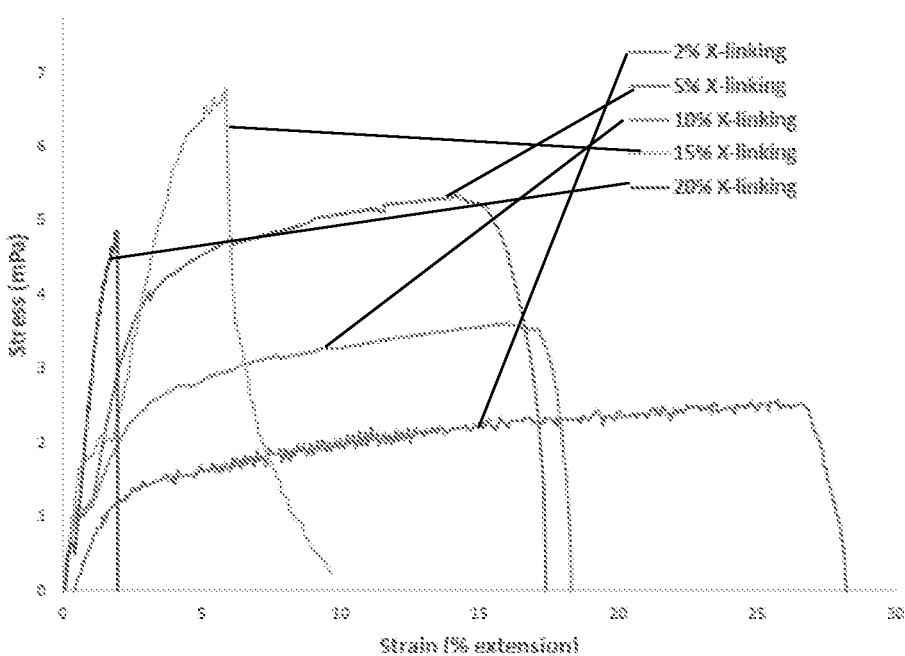
Figure 2:
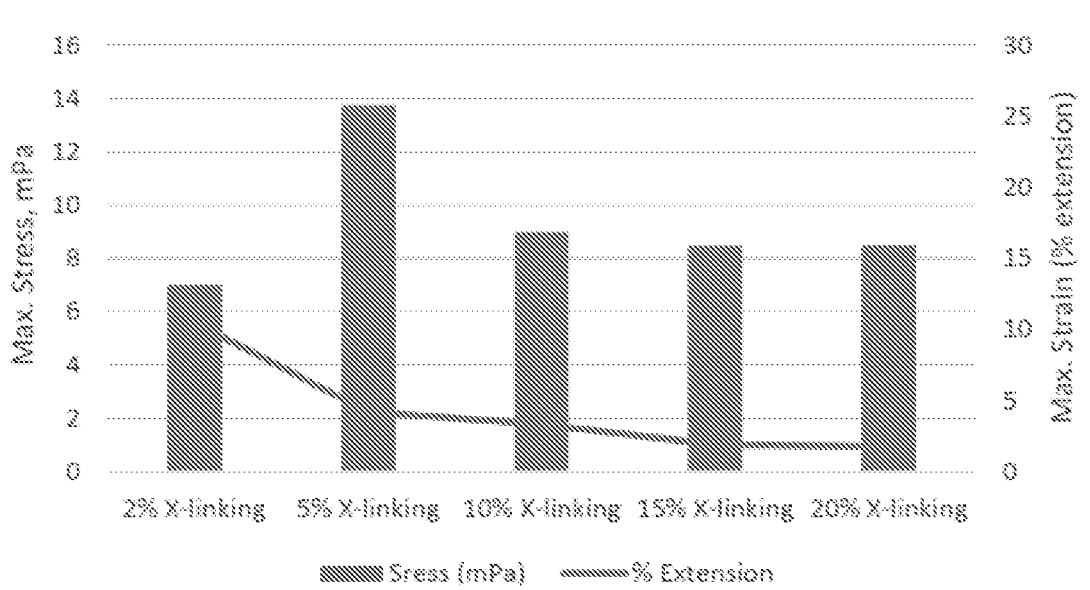
FIGS. 2a and 2b show the effect of divanillin levels on tensile strength and elongation of 200 micron-thick starch films after curing (curing was performed by incubation of films at 150° C. for 5 minutes), as bar graph and as stress-strain curve, respectively.
Figure 2B:
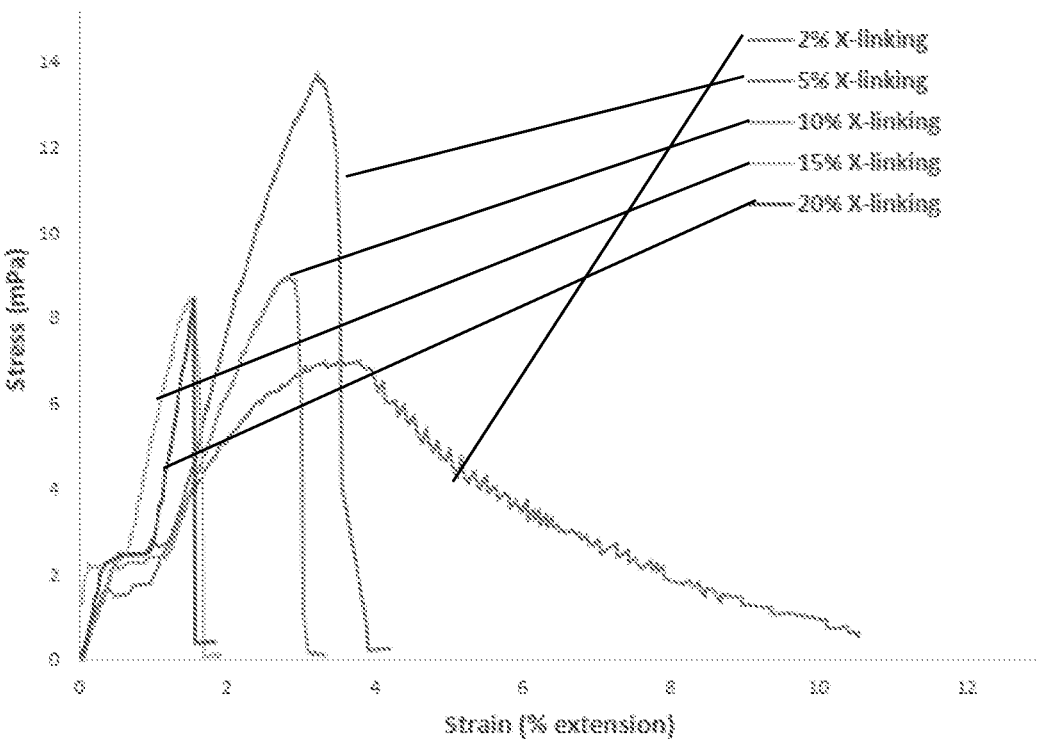
Figure 3:
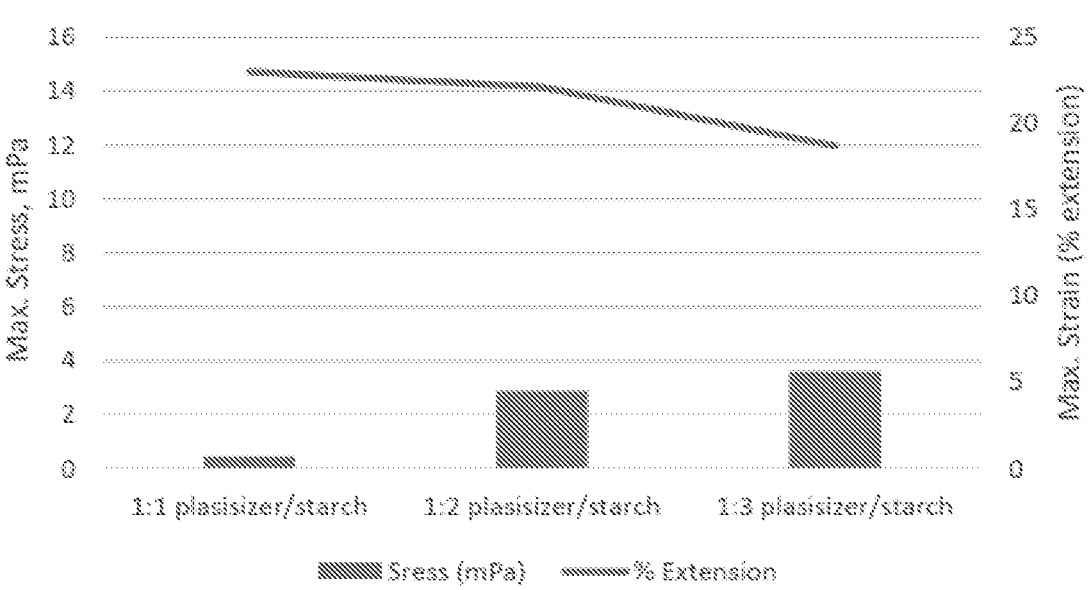
FIG. 3 demonstrates the plasticizer (glycerol) effect on tensile strength and elongation of 200 micron-thick starch films without curing.
Figure 4:
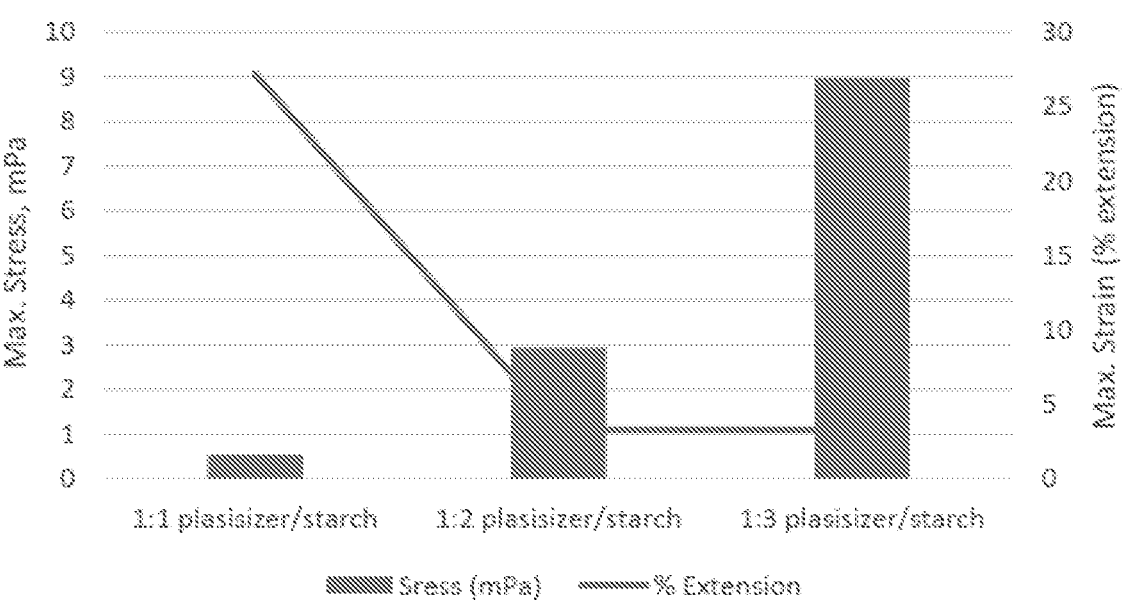
FIG. 4 demonstrates the plasticizer (glycerol) effect on tensile strength and elongation of 200 micron-thick starch films after curing (curing was performed by incubation of films at 150° C. for 5 minutes).

In the FIGS. 1-4, the left axis title "Max Stress, mPa" in the FIGS. 1a, 1b, 3 and 4, indicates the maximum stress for the tested specimen, expressed in milli-Pascals. The right axis title "Max. Strain (% extension)" in the FIGS. 1a, 1b, 3 and 4, indicates the maximum obtained strain of the specimens, expressed in elongation percentage from the original dimensions. The legend reference to the bars in the FIGS. 1a, 1b, 3 and 4, "Sress (mPa)" refers to the measurements expressed by the left axis, and the legend reference in the FIGS. 1a, 1b, 3 and 4, "% Extension" refers to the measurement expressed by the right axis, denoted as the solid line. The bottom axis labels of the FIGS. 1a, 2a, and also the legend references in the FIGS. 1b and 2b, "2%

X-linking", "5% X-linking", "10% X-linking", "15% X-linking", "20% X-linking", denotes specimens that contained 2%, 5%, 10%, 15%, or 20%, respectively, by mass, of crosslinking agent relative to the polymer. The bottom axis legends in the FIGS. 3 and 4, "1:1 plasisizer/starch", "1:2 plasisizer/starch", and "1:3 plasisizer/starch", refer to the compositions containing the ratio between the plasticizer and starch as 1:1, 1:2 and 1:3, respectively.

Figure 5:
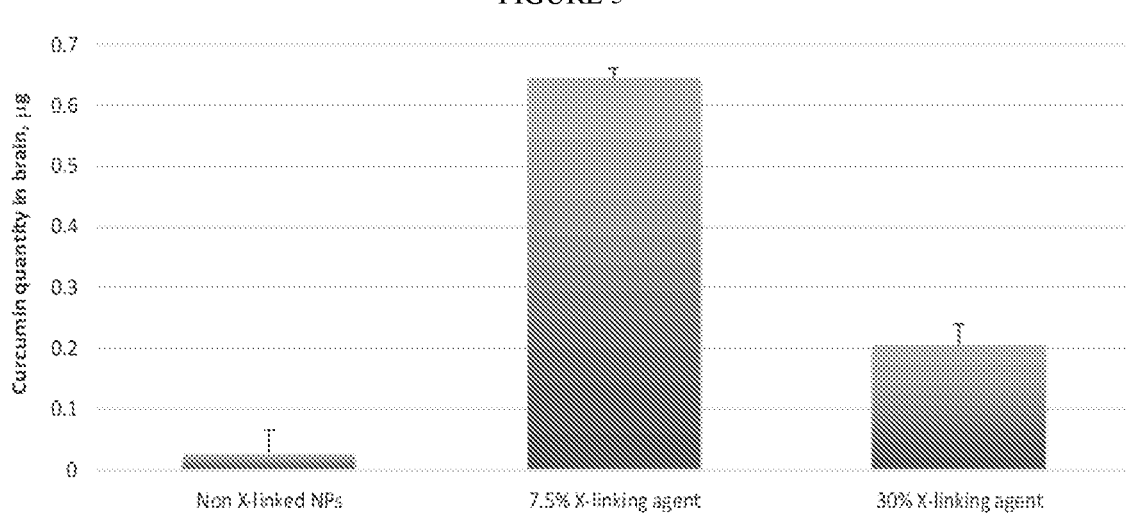

FIG. 5 depicts the curcumin accumulation in rats' brain 1 hour after internasal administration of a 6.5 μg dose. The vertical axis title "Curcumin quantity in brain, μg" denotes the quantity of curcumin detected in the bran, expressed in micrograms. The horizontal axis labels "Non X-linked NPs", "7.5% X-linking agent", and "30% X-linking agent" denote specimens that are non-crosslinked nanoparticles, nanoparticles containing the polymer with 7.5% of crosslinking agent, and nanoparticles containing the polymer with 30% of crosslinking agent, respectively, by weight of the polymer.

Figure 6:
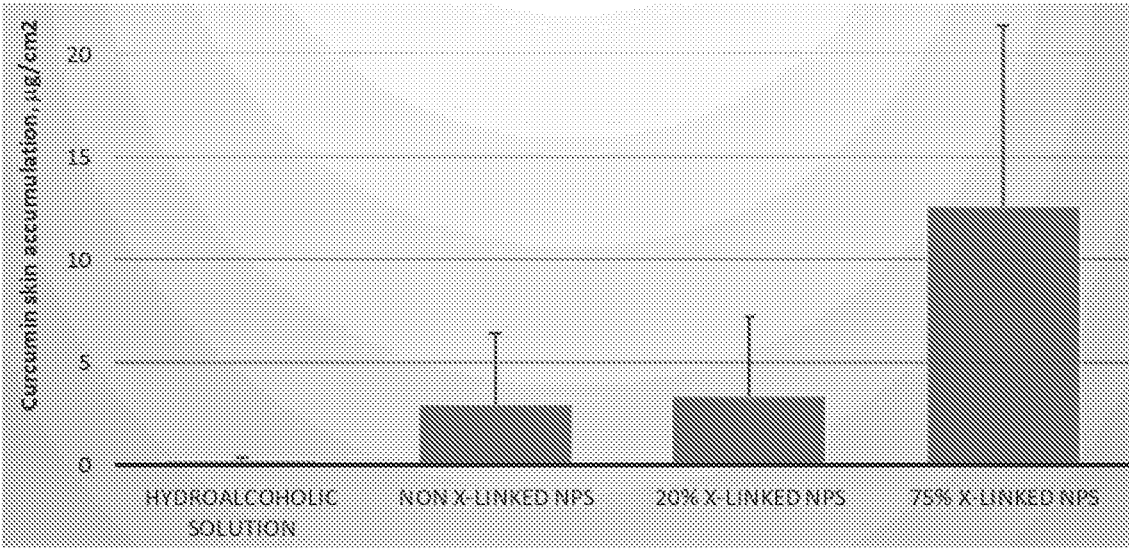

FIG. 6 depicts curcumin penetration into rat's skin 6 hours after application. The vertical axis title "Curcumin skin quantity, μg/cm2" denotes the quantity of curcumin detected in the skin, expressed in micrograms per square centimeter. The horizontal axis labels "HYDROALCOHOLIC SOLUTION", "NON X-LINKED NPS", "75% X-LINKING AGENT", and "20% X-LINKING AGENT" denote specimens that curcumin hydroalcoholl solution, non-crosslinked nanoparticles, nanoparticles containing the polymer with 75% of crosslinking agent, and nanoparticles containing the polymer with 20% of crosslinking agent, respectively, by weight of the polymer.

Figure 7A:
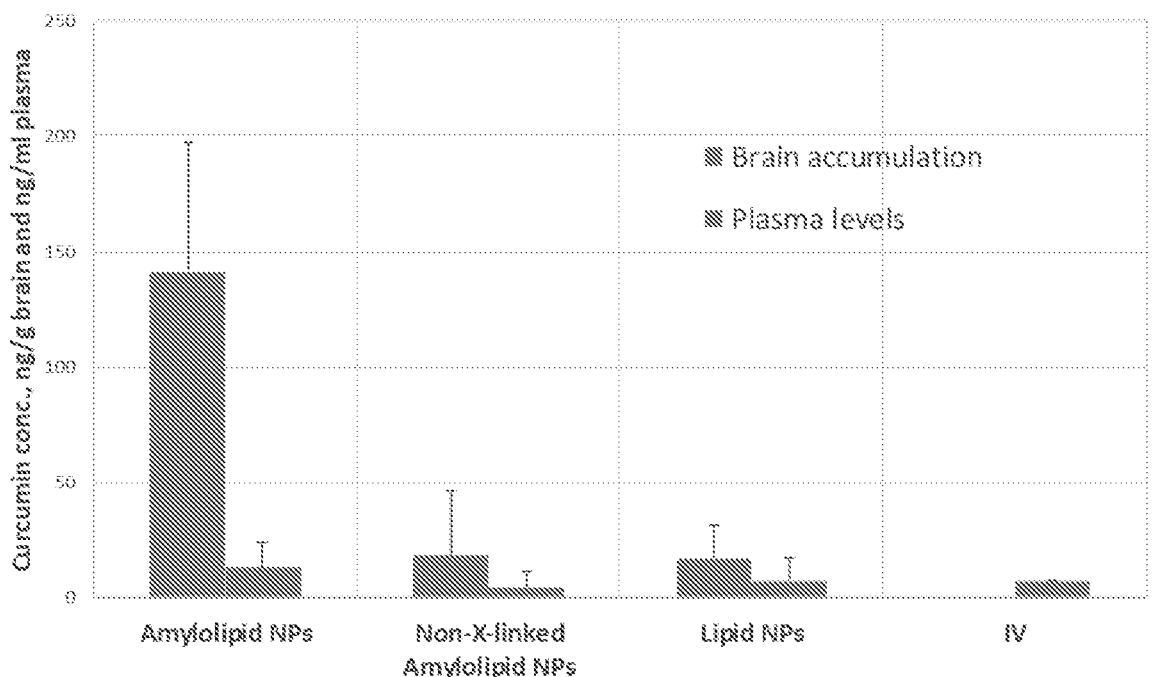
Figure 7B:
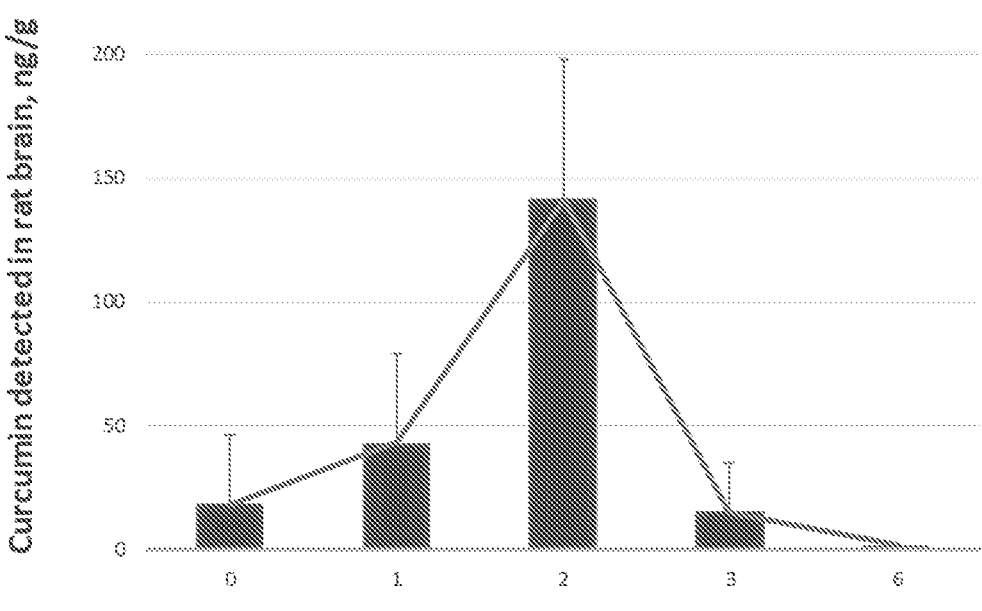

FIG. 7 (A) depicts the curcumin concentration in the brain following intranasal administration of amylolipid nanovesicles (ALNs) in rats; the vertical axis title "Curcumin conc., ng/g in brain, and ng/ml plasma" denotes the concentrations of curcumin detected in the brain, expressed as nanograms of curcumin per gram tissue, and curcumin concentration in plasma, expressed in nanograms per milliliter, respectively. The horizontal axis labels "Amylolipid NPs", "Non-X-linked Amylolipid NPs", "Lipid NPs", and "IV", denote specimens of nanoparticles comprising the crosslinked polymeric and also lipidic component, non crosslinked polymeric and also lipidic component, only lipidic component, and an intravenous administration, respectively. The left bars denote accumulation in brain ("Brain accumulation" label), and the right bars denote plasma concentration ("Plasma levels" label). FIG. 7B) depicts the relationship between the brain concentrations of curcumin and the crosslinking degree of the ALNs. The vertical axis title "Curcumin detected in the rat brain, ng/g" denotes the concentrations of curcumin detected in the rat brain, expressed as nanograms of curcumin per gram tissue. The horizontal axis label "Crosslinking level, % of starch", denotes the crosslinking degree as expressed in weight percent of the crosslinking agent relative to the weight of the polymer.

Figure 8:
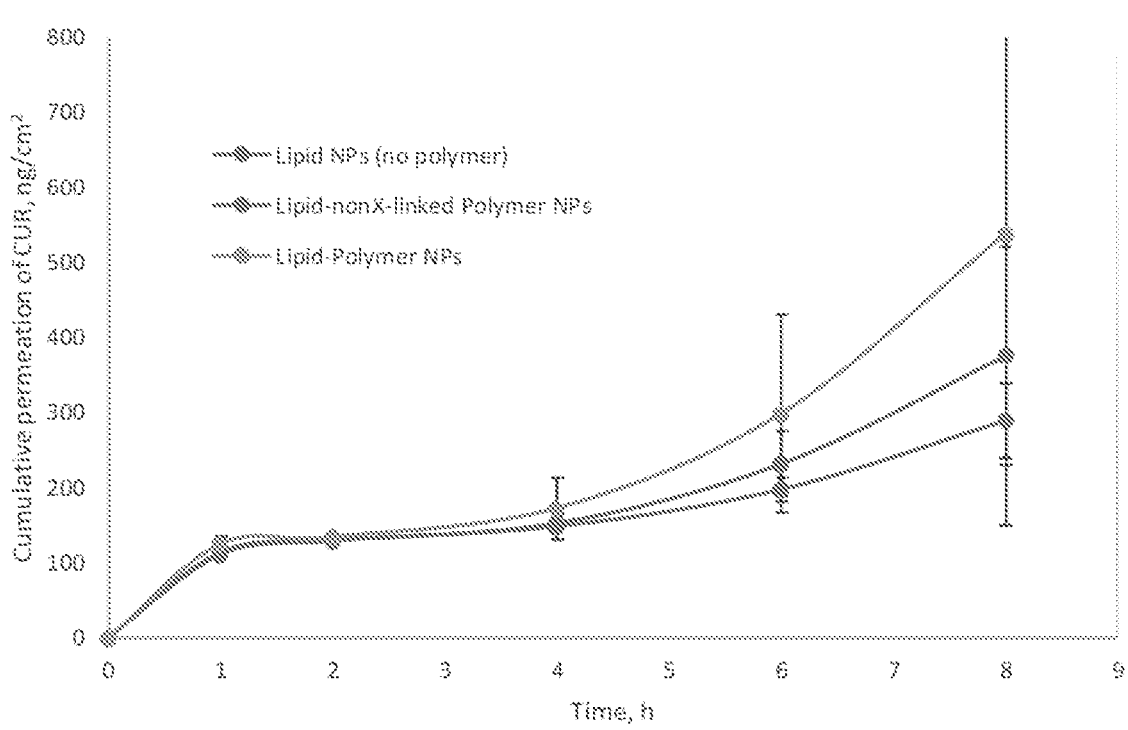

FIG. 8 depicts the curcumin permeation via rat's skin. The vertical axis title "Cumulative permeation of CUR, ng/cm2" denotes the cumulative amount of curcumin permeated through rats' skin, expressed as nanograms of curcumin per square centimeter of skin. The horizontal axis label "Time, h", denotes the time elapsed from the initiation of the experiment, expressed in hours. The curve labels "Lipid NPs (no polymer)", "Lipid-nonX-linked Polymer NPs", and "Lipid-Polymer NPs" denotes the concentrations obtained from the specimens with lipid nanoparticles with no polymer according to the invention (seen lowest at 8 hours), lipid nanoparticles with non-crosslinked polymer according to the invention (seen as the median value at 8 hours), and nanoparticles with cross-linked polymer according to the invention (seen highest at 8 hours).

Figure 9:
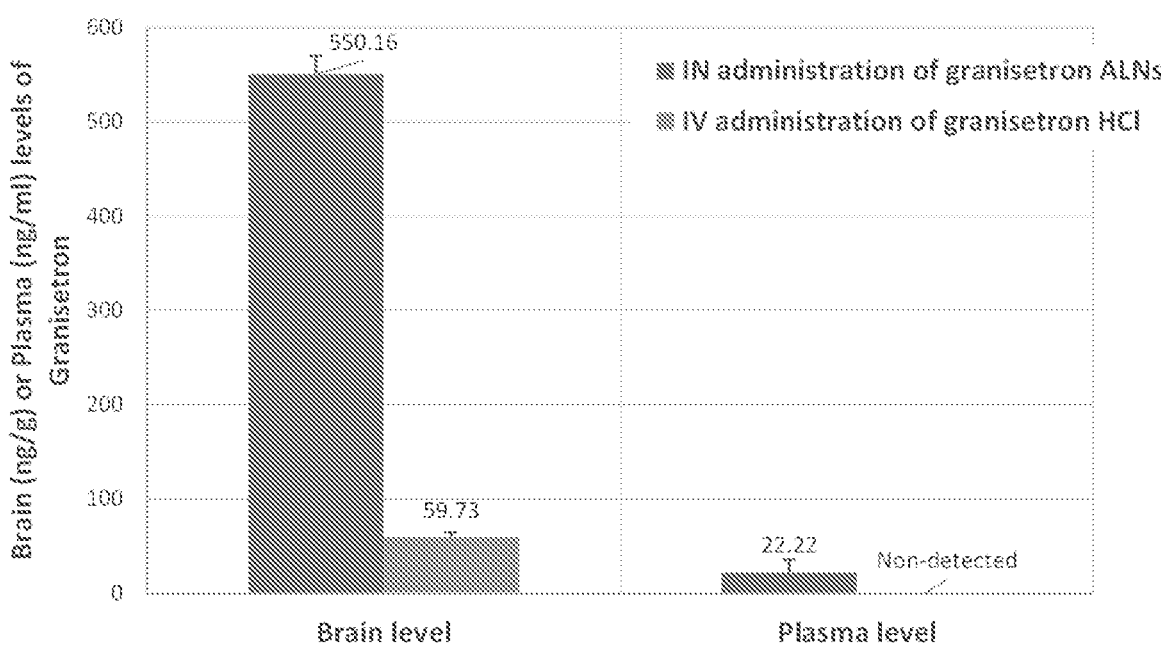

FIG. 9 depicts the granisetron distribution in the brain and plasma one hour after administration. The vertical axis title "Brain (ng/g) or Plasma (ng/ml) levels of Granisetron" denotes the concentrations of granisetron detected in the brain, expressed as nanograms of granisetron per gram tissue, and granisetron concentration in plasma, expressed in nanograms per milliliter, respectively. The horizontal axis labels "Brain level" and "Plasma level", denote the concentrations in the brain and in the plasma, respectively. The left bars denote accumulation in brain ("IN administration of granisetron ALNs" label), and the right bars denote plasma concentration ("IV administration granisetron HCl" label). The values labels denote the average concentrations obtains, with the label "Non-detected" denoting that no drug was detected.

Figure 10:
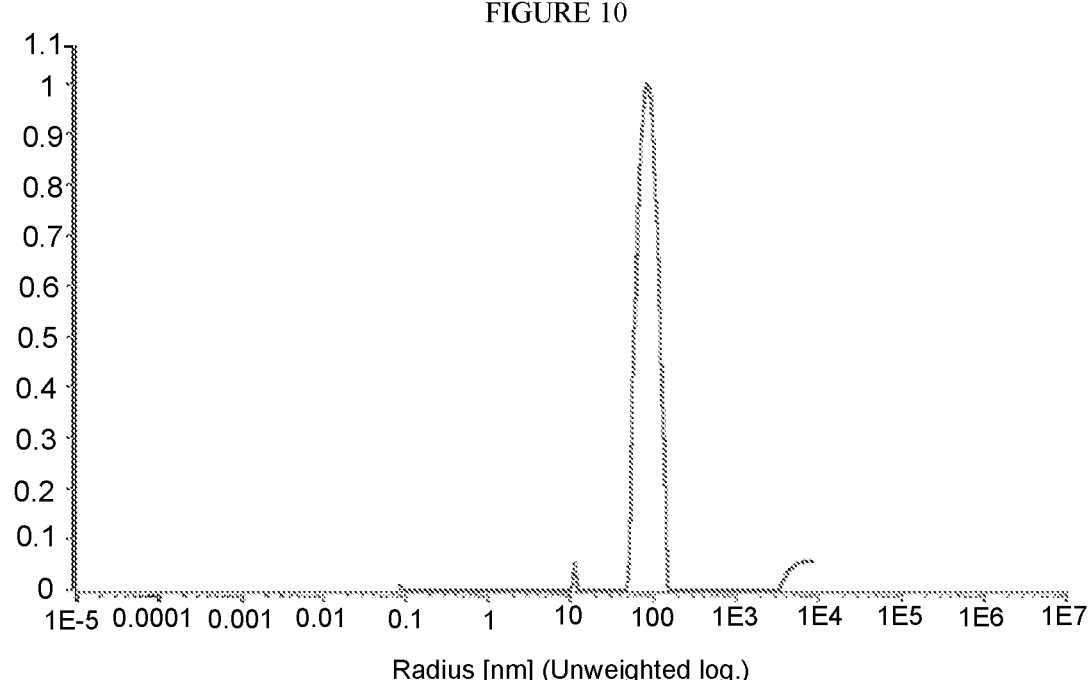

FIG. 10 depicts a DLS measurement of the particles comprising granisetron.

Figure 11A:
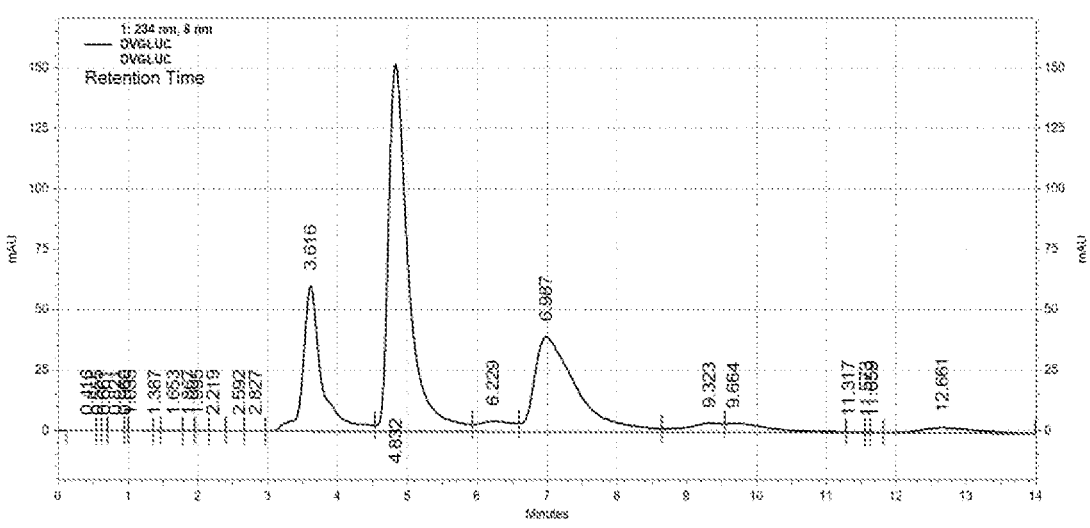
Figure 11B:
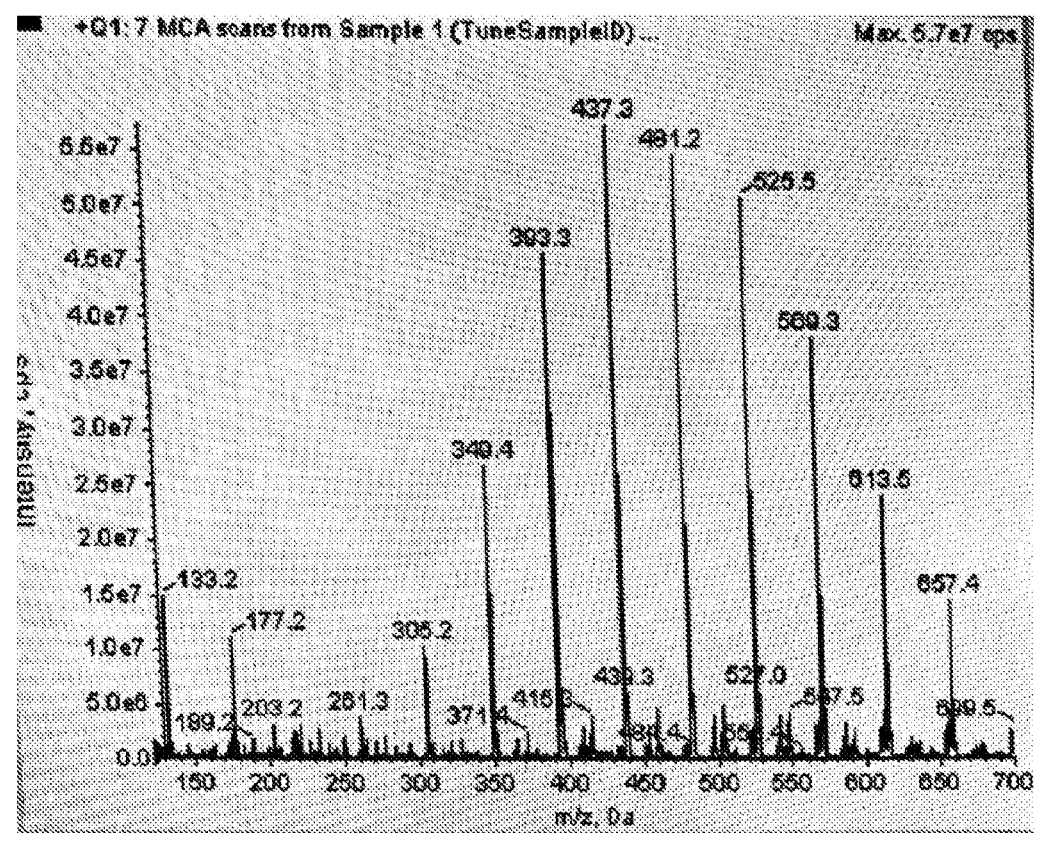
Figure 11C:
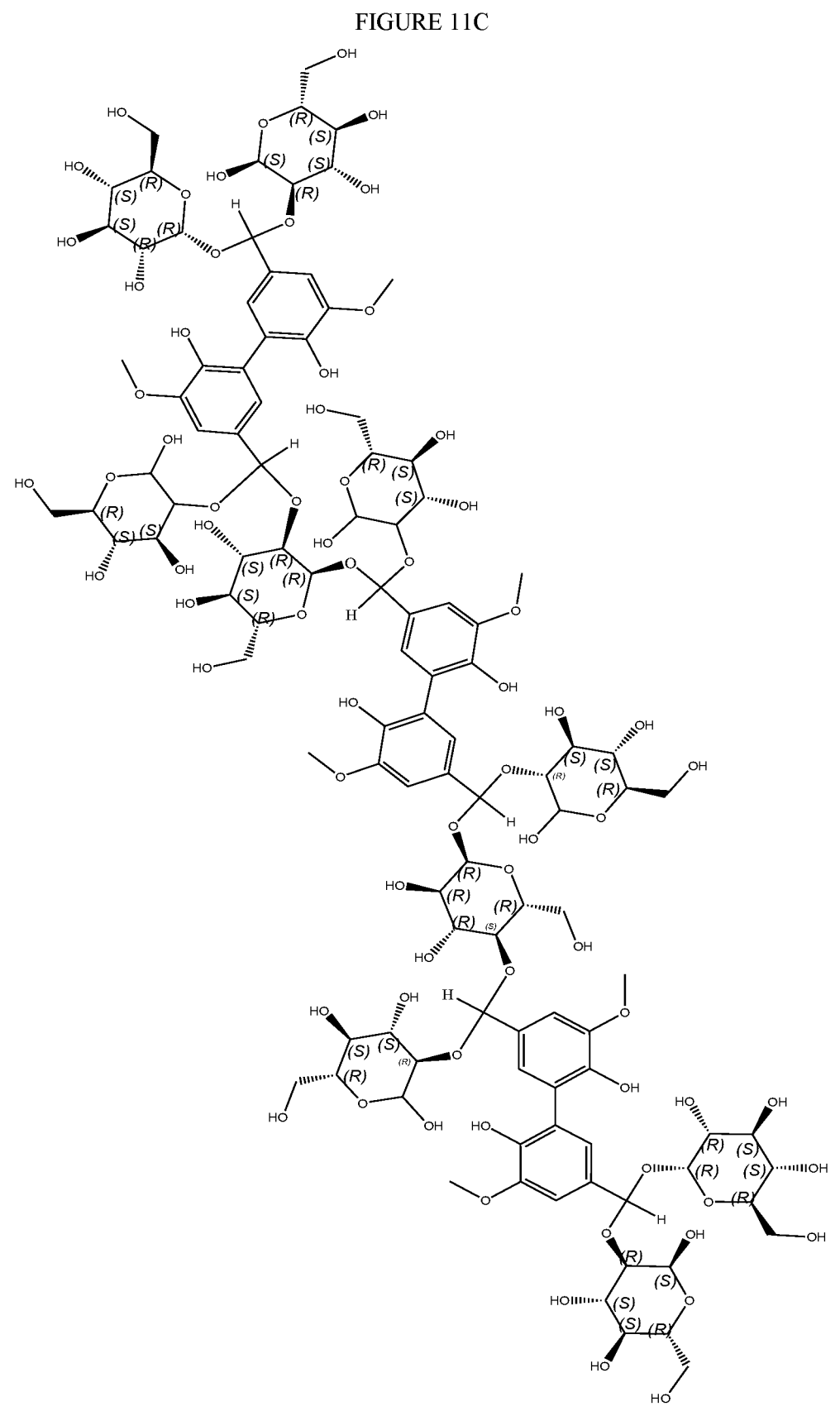

FIG. 11 *a*) depicts a chromatogram of a reaction mixture of dispersed divanillin with glucose, 11 *b*) depicts the mass spectrum of the main peak of 12*a*; and 11 *c*) depicts suggested structure of divanillin-glucose adduct.

Figure 12:
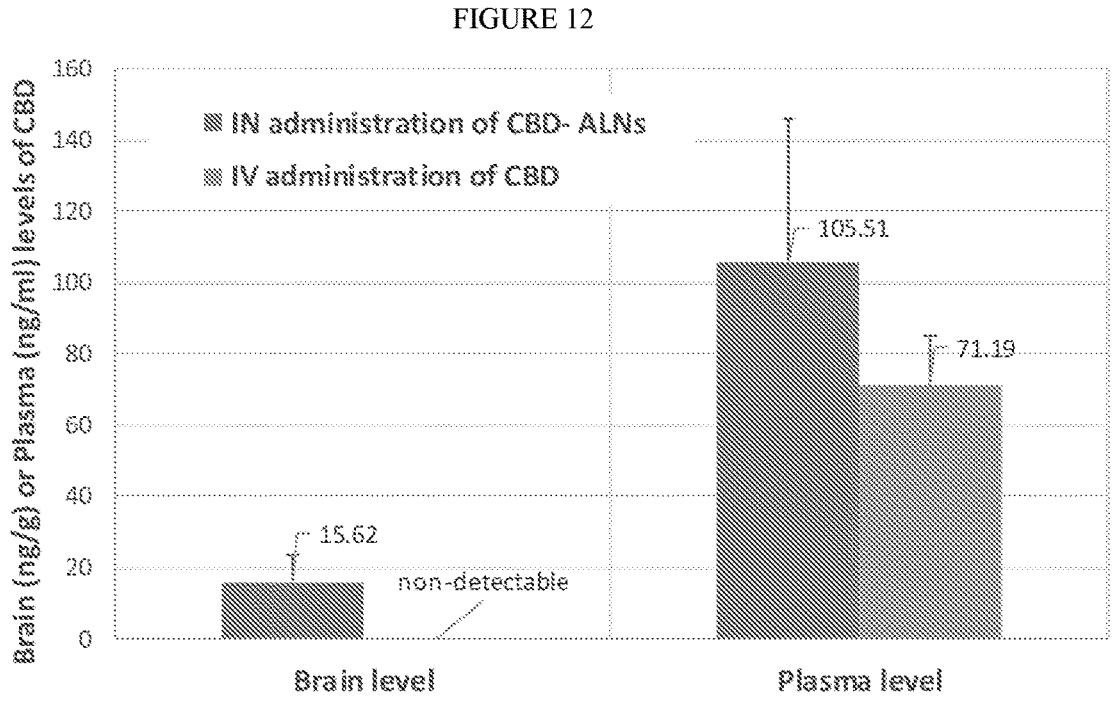

FIG. 12 depicts cannabidiol distribution (brain and plasma) 1 hour after intranasal and intravenous administrations of CBD-containing ALNs. The vertical axis title "Brain (ng/g) or Plasma (ng/ml) levels of CBD" denotes the concentrations of cannabidiol detected in the brain, expressed as nanograms of CBD per gram tissue, and CBD concentration in plasma, expressed in nanograms per milliliter, respectively. The horizontal axis labels "Brain level" and "Plasma level", denote the concentrations in the brain and in the plasma, respectively. The left bars denote accumulation in brain ("IN administration of CBD-ALNs" label), and the right bars denote plasma concentration ("IV administration CBD" label). The values labels denote the average concentrations obtains, with the label "Non-detectable" denoting that no drug was detected.

Figure 13:
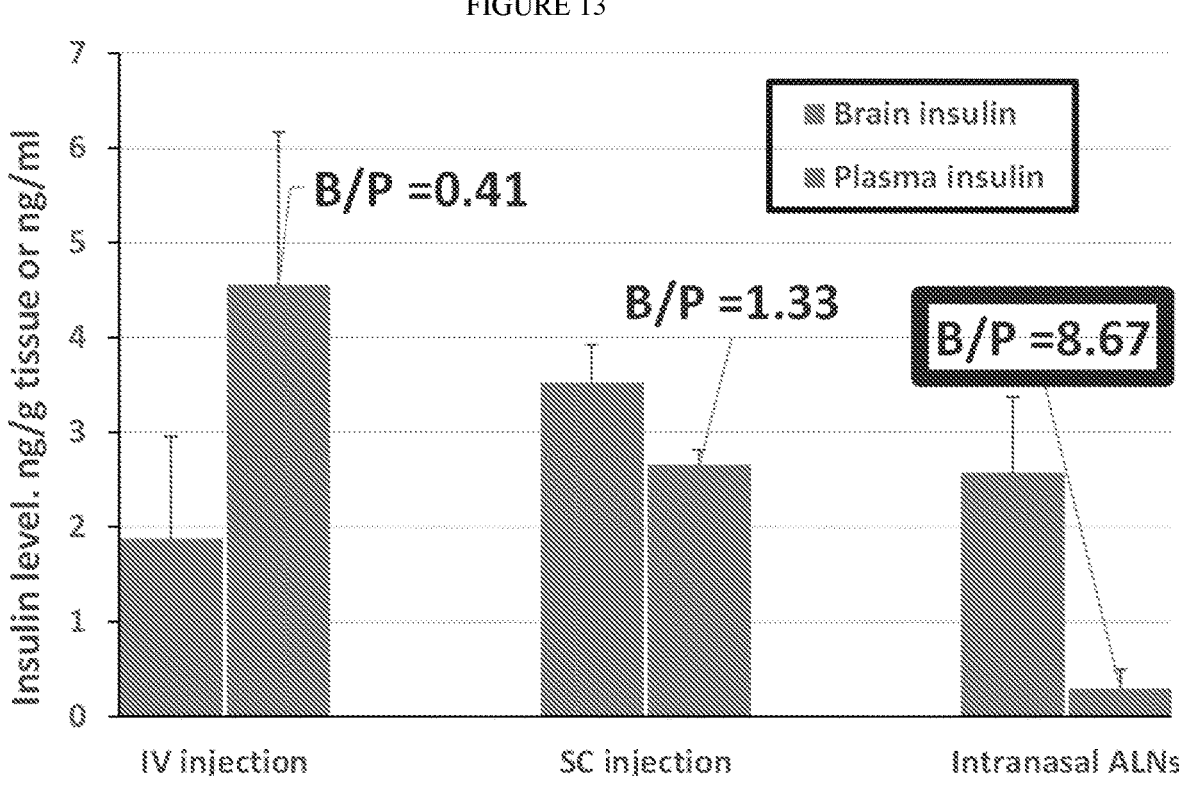

FIG. 13 depicts insulin distribution (brain and plasma) 1 hour after intranasal, subcutaneous and intravenous administrations of insulin-containing ALNs. The vertical axis title "Insulin level. ng/g tissue or ng/ml" denotes the concentrations of insulin detected in the brain, expressed as nanograms per gram tissue, and concentration in plasma, expressed in nanograms per milliliter, respectively. The horizontal axis labels "IV injection", "SC injection" and "Intranasal ALNs", denote the concentrations in the brain (left bars, "Brain insulin" label) and in the plasma (right bars, "Plasma insulin" label), after the intravenous and subcutaneous administration of insulin, and after intranasal administration of insulin-loaded nanoparticles according to the invention, respectively. The values labels denote the brain-to-plasma ratio, with the boxed value corresponding to the administration of the nanoparticles according to the invention.

DETAILED DESCRIPTION

The present invention provides a biodegradable composition comprising polysaccharide, preferably a starch, crosslinked with an aromatic dialdehyde. In general, a non-crosslinked starch has limited industrial application due to poor mechanical properties as well as high water absorption capacity, which often makes starch susceptible towards bacterial growth. However, it was surprisingly found that the crosslinking of starch with an aromatic dialdehyde enhances the mechanical strength and increases water resistance of said starch. According to the principles of the present invention, depending on its crosslinking degree, the stability of the starch-based composition as described above in an aqueous media is at least one week. Thus, a composition of matter comprising a polysaccharide chemically cross-linked by an aromatic dialdehyde constitutes a first aspect of the invention.

In some embodiments, the polysaccharide is crosslinked by an aromatic dialdehyde. The polysaccharide is usually a water-soluble polymer. The polysaccharide may usually be selected from the group consisting of corn starch, chitosan, xanthan gum, guar gum, an alginate, and a cellulose or cellulose derivatives. When cellulose derivatives are used, they are preferably soluble in water. The water-soluble cellulose derivatives include methyl cellulose, hypromellose, hydroxyethyl cellulose, and hydroxypropyl cellulose. In some preferred embodiments, the polysaccharide is a starch. The starch is a polymeric carbohydrate consisting of glucose units connected by α-glycosidic bonds, having a linear or branched structure (termed "amylose" and "amylopectin", respectively), dependent on its source. Generally, any source of starch may be suitable for utilizing in the present invention. The preferred sources of starch are corn (maize) and potato.

The aromatic dialdehyde is usually a bio-based, non-toxic dialdehyde. Preferably, the aromatic dialdehyde is divanillin, di-cinnamaldehyde, di-coniferylaldehyde (coniferylaldehyde is a flavonoid isolated from cinnamon), di-coumaraldehyde, or di-sinapaldehyde (sinapaldehyde is enzymatically formed from coniferylaldehyde). Divanillin is 3-(5-formyl-2-hydroxy-3-methoxyphenyl)-4-hydroxy-5-methoxybenzaldehyde, having a CAS number 2092-49-1. Di-cinnamaldehyde is made of cinnamaldehyde [(2E)-3-phenylprop-2-enal; CAS No. 14371-10-9]. Di-coniferylaldehyde is made of coniferyl aldehyde [(E)-3-(4-hydroxy-3-methoxyphenyl)prop-2-enal; CAS No. 458-36-6]. Di-coumaraldehyde is made of coumaraldehyde [(E)-3-(4-hydroxyphenyl)prop-2-enal; CAS No. 20711-53-9]. Di-sinapaldehyde is made of sinapaldehyde [(E)-3-(4-hydroxy-3,5-dimethoxyphenyl)prop-2-enal; CAS No. 4206-58-0].

In a currently preferred embodiment, the aromatic dialdehyde utilized for polysaccharide (e.g. starch) crosslinking is divanillin. Other preferred polysaccharides include alginic acid and its salts, and cellulose derivatives, e.g. hydroxypropyl cellulose.

The biodegradable composition of the invention may be manufactured via several different processes and the final product's shape, mechanical strength and other properties can be tailored to the intended use of the material.

In one aspect, the biodegradable composition of the invention is in the form of polymeric sheets. These polymeric sheets may be manufactured in form of films, e.g. by a solution casting of the cross-linked composition. According to the principles of the present invention the biodegradable sheets of the invention may have any suitable thickness, determined by their final application. Any thickness between about 15 microns to about 5 mm may be produced, preferably between 100 and 1500 microns.

In a further aspect, the biodegradable composition of the invention is in the form of nano-sized particles. Depending on their composition and other constituents, the nano-sized particles may have a homogeneous phase of the polymeric biodegradable composition of the invention, forming the particle. The particles may also have a homogenous phase of the polymeric biodegradable composition mostly on the surface of the particle; in these cases a term "nanocapsule" or the like could be used.

When the polysaccharide is starch, the nano-sized particles may also comprise lipids, as described in greater detail below, in which case the nano-sized particles may also be termed as Amylo-Lipid Nanovesicles (or as ALN acronym).

The amount of the aromatic dialdehyde relative to the amount of the polymer, e.g. the cross-linking degree, may vary according to the required final properties of the composition. Where hard material is needed, the crosslinking degree may be high. Generally, the crosslinking degree may vary between about 0.5% wt of the weight of polysaccharide, to as high as about 80% wt of the weight of the polysaccharide. Preferably, the crosslinking degree is between 0.5% wt and 20% wt, particularly when the composition is in form of polymeric films (e.g. sheets). Preferably, the crosslinking degree may be between about 1% and about 10%, particularly for the polymeric sheets. When the composition is in form of nano-sized particles, the cross-linking degree may be from about 0.5% wt to about 20 wt %, e.g. between about 1% wt to about 3% wt, particularly when the nano-sized particles are lipid-polymer particles, as described below. The nano-sized particles may also comprise the polysaccharide cross-liked to a higher degree, e.g. between about 6% wt to about 10% wt, particularly when the particles are manufactured by nanoprecipitation without lipids. The suitable cross-linking degree may be adapted according to the need of a particular formulation and application.

The term "nanoparticle" is used herein generically to any nano-sized particles or vesicles with a variety of internal structures and components' distribution, unless the context clearly indicates otherwise, provided that the nanoparticles comprise a polysaccharide cross-linked with an aromatic dialdehyde. The nano-sized particle has a particle size in the range of nanometers, e.g. between 10 and 950 nm. Preferably, the nano-sized particles have a particle size between 50 and 250 nm.

Thus, in some embodiments, the present invention provides a composition of matter in form of nanoparticles. The composition may be formulated into a pharmaceutically acceptable formulation, e.g. a drug delivery system. The drug delivery system may comprise the biodegradable nanoparticles comprising a polysaccharide chemically cross-linked by an aromatic dialdehyde, and have a biologically active ingredient therein. In further embodiments, the present invention provides a biodegradable composition in the form of capsules, preferably nano-sized capsules, i.e. particles having a core-shell-like structure. In these structures, the shell, i.e. the outermost part of the capsule, usually comprises the biodegradable composition of the invention, and the core, i.e. the inner part of the capsule, comprises a separate phase. Usually the separate phase of the capsule is a lipophilic phase. Alternatively, the nano-sized capsules may have a multi-phasic structure, with the biodegradable composition of the invention being the matrix wherein lipidic phase droplets are distributed. The nano-sized particles and/or capsules usually further comprise a biologically active agent as described below. Upon the insertion of the drug delivery system into the body, the active biological agent is released from the nanoparticles of the invention and the nanoparticles degrade by inter- and intracellular body fluids, and by specific and non-specific enzymes at a rate and extent, which is individual to each system's composition and administration mode. As demonstrated in the examples' section below, the composition may be adapted in such a way, e.g. via the cross-linking ratio, as to control the extent of brain permeation of the nanoparticles, following intranasal administration, or to control the skin penetration and permeation following topical administration.

Thus, according to the principles of the invention, the biodegradable nanoparticles and/or capsules can be formulated for a topical delivery, systemic administration, oral administration, sublingual administration, or an intranasal administration. Therefore, in a separate aspect, the present invention provides the use of biodegradable carriers of the invention as a drug delivery system. The delivery system comprises an aromatic dialdehyde crosslinked polysaccharide, preferably a starch, and a biologically active agent, given that there is no appreciable chemical reactivity of the aromatic dialdehyde towards said biologically active agent. The drug delivery system of the present invention may enhance the bioavailability and increase the stability and efficacy of the biologically active agent in a subject, in comparison to the same biological active agent given without the drug delivery system of the invention in the same dosage and conditions. Particularly, when the delivery system comprises a nano-sized particles and is administered as intranasal delivery (i.e. as a spray into the nose), the delivery system may enable the delivery of the biologically active material into the brain, providing brain concentrations that are at least 150 percent higher than the concentration in the brain obtained by other route of administration. The brain concentrations may be measured in a test non-human mammal subjects, as known in the art.

In some embodiments, nanoparticles further comprise a biologically active agent. The term "biologically active" as used herein and in the claims is interchangeable with the term "bioactive material" and the like, and refers to a substance which is of a natural or synthetic origin and which have a positive influence on at least some human biological systems such as balancing nutrients levels and/or preventing diseases and deficiencies, e.g. in the present invention. Some preferred examples for a biologically active ingredients include curcumin, cannabidiol, granisetron, and insulin.

The bioactive material for use in the present invention is substantially stable in presence of the aromatic dialdehyde used for crosslinking of the polysaccharide. This means that in presence of a dispersed polysaccharide, e.g. dissolved polysaccharide, no more than 10% of the total drug dose chemically react with the aromatic aldehyde, preferably less than 5%, and further preferably less than 1%, and less than 0.5%.

Further examples of biologically active agents include a food supplement, an antibiotic, a further cannabinoid apart from cannabidiol, an analgesic, and may also be an antihistaminic drug, anti-inflammatory agent, psychoactive agent, antipsychotic agent, neurological active agent, antiparkinsonian or anti-amyloid agent, cholinergic or adrenergic drugs, anti-cancer drugs, anti-emetic drugs, drugs affecting cardiovascular function (e.g., antihypertensive drugs), hormones, vitamins, ocular or otic drugs, dermatological and cosmetic agents, polypeptide, protein-based drug, antiviral agent, anti-neoplastic agent, sex hormone, corticosteroid, anti-epileptic, anti-spasmolytic, sedative, anti-depressant, serotonin antagonist, anorexigenic agents such as glucagon-like peptide, gastric inhibitory polypeptide, amylin, leptin, melanocortin 4 agonist, pancreatic polypeptide, oxynto-modulin, cholecystokinine, etc., amino acid, amino sugar, anorectic, anti-allergic drug, anti-cholinergic, parasympathomimetic, antihypertensive agent, antiangina drug, narcotic, narcotic antagonist, bronchodilators, blood factor, bone metabolism agent, protease inhibitor, dye, diagnostic agent, or any combination thereof.

The biologically active agent may be present on the surface or in the core of nanoparticles, e.g. nanospheres, nanocapsules, micro- or sub-microparticles, or inside droplets of a nanoemulsion. As demonstrated in the examples' section below, the molecular weight of the bioactive agent is not limited to a particular group of compounds. In the practice of this invention a low-molecular, medium-molecular or high-molecular drug or a biologically active agent may be used.

The concentrations of the biologically active compounds may vary, depending on the carriers, e.g. dosage form, wherein they are incorporated, from about 0.001% (10 µg/g) to about 20% (i.e. 200 mg/g), preferably, 0.1%-10% by weight. The carriers may be pharmaceutically and/or cosmetically acceptable carriers, such as liquids, cream, gel, spray, aerosol, foam, discs, films, pellets, or patches. The biologically active material can be dissolved, dispersed or aggregated in the dosage form, comprising the composition of a polysaccharide crosslinked with an aromatic dialdehyde.

In some embodiments, the biologically active agent incorporated into the delivery systems of the invention may be selected from a food supplement, antibiotic, cannabinoid, analgesic, antihistaminic drug, anti-inflammatory agent, psychoactive agent, antipsychotic agent, neurological active agent, antiparkinsonian or anti-amyloid agent, cholinergic or adrenergic drugs, anti-cancer drugs, anti-emetic drugs, drugs affecting cardiovascular function (e.g., antihypertensive drugs), hormones, vitamins, ocular or otic drugs, dermatological and cosmetic agents, polypeptide, protein-based drug, antiviral agent, anti-neoplastic agent, sex hormone, corticosteroid, anti-epileptic, anti-spasmolytic, sedative, anti-depressant, serotonin antagonist, amino acid, amino sugar, anorectic, anti-allergic drug, anti-cholinergic, parasympathomimetic, antihypertensive agent, antiangina drug, narcotic, narcotic antagonist, bronchodilatorsor, blood factor, bone metabolism agent, protease inhibitor, dye, diagnostic agent, or any combination thereof. More specifically, the biologically active agents can be cannabinoid such as tetrahydrocannabinol, cannabidiol, cannabinoid acid form, cannabinol, cannabigerol, *Cannabis* entourage components, cannabinoid combinations, or *Cannabis* extracts. Also the biologically active agents can be polypeptides or protein-based drugs or hormones such as insulin, glucagons, follicle-stimulating hormone, growth hormone, vasopressin, adenocorticotropic hormone [ACTH], oxytocin, thyrotropin releasing hormone [TRH], luteinizing hormone releasing hormone [LHRH agonists such as leuprolide], and other analogs, parathyroid hormone, anticancer and antiviral agents such as interferons (e.g., alpha-2a,b-interferon, beta-interferon), anti-neoplastic agents (e.g., carmustine, doxorubicin, fluorouracil, cisplatin, cyclophosphamide, busulfan, carboplatin, leuprolide, megestrol, lomustine, levamisole, flutamide, etoposide, cytaranine, mitomycin, nitrogen mustard, paclitaxel, actinomycin, tamoxifen, vinblastine, vincristine, thiotepa, chlorambucil, etc.), sex hormones (e.g., progesterone, estradiol-17-beta, testosterone, norethindrone, levonorgestrel, ethinylestradiol, FSH, luteinizing hormone [LH], etc.), corticosteroids (e.g., hydrocortisone, prednisolone, budesonide, etc.), local anesthetics (lidocaine, prilocaine, benzocaine, tetracaine, etc.), neurologically effective drugs including anti-epileptics/anti-spasmolytics (e.g., benzodiazepines such as diazepam, clonazepam, lorazepam, etc.), and sedatives/tranquilizers (e.g., mirtazapine, trazodone, amobarbital, pentobarbital, secobarbital, alprazolam, clonazepam, diazepam, flunitrazepam, lorazepam, triazolam, chlorpromazine, fluphenazine, haloperidol, loxapine, perphenazine, prochlorperazine, thiothixene, trifluoperazine, clozapine, olanzapine, quetiapine, risperidone, ziprasidone, valerian, kava-kava, chloral hydrate, diethyl ether, eszopiclone, glutethimide, meprobamate, zolpidem, ramelteon, methyprylon, etc.), anti-depressants (e.g., imipramine, amoxapine, butriptyline, fluoxetine, sertraline, venlafaxine, citalopram, paroxetine, fluvoxamine, escitalopram, duloxetine, bupropion, amitriptyline, dosulepin, isocarboxazid, nialamide, phenelzine, selegiline, toloxatone, tranylcypromine, harmaline, iproclozide, iproniazid, clomipramine, desipramine, dibenzepin, dothiepin, Doxepin, iprindole, lofepramine, melitracen, nortriptyline, opipramol, protriptyline, trimipramine, etc.), anti-emetics (e.g., dopamine antagonists—metoclopramide, clopromazine, promethazine, domperidone, etc., serotonin antagonists—granisetron, ondansetron, etc., etc., antihistamines—cyclizine, promethazine, meclizine, hydroxyzine, etc., canabinoids—marinol, *Cannabis*, etc., others—trimethobezamide, emetrol, etc.), amino acids, amino sugars (e.g., glucosamine, etc.), antibiotics (e.g., gentamycin, penicillin derivatives, streptomycin, aminoglycosides, cephalosporine, erythromycin, tetracycline, etc.), anti-inflammatory agents (steroidal—e.g., hydrocortisone, prednisone, prednisolone, triamcinolone, dexamethasone, betamethasone, beclomrthasone, clobetasone, clobetasol, budesonide, amcinonide, cortisone, desonide, flucinonide, flucinolone, methylprednisolone, mometasone, tixocortol, diflucortolone, diflorasone, halometasone, halcinonide, flucortolone, desoximetasone, etc., and nonsteroidal—e.g., acetylsalicylic acid, sasalate, ibuprofen, ketoprofen, naproxen, fenoprofen, flurbiprofen, oxaprozin, diclofenac, indomethacin, sulindac, tolmetin, piroxicam, meloxicam, mefenamic acid, nabumetone, etodalac, ketorolac, celecoxib, valdecoxib, rofecoxib, etc.), anorectics (e.g., benzphetamine, diethylproprion, tepanilfenfluramine, mazindol, phendimetrazine, phentermine, etc.), anti-allergic drugs (e.g., antihistamines such as diphenhydramine, histamine, cromoglycate, meclizine, dimethindene maleate, etc.), anti-cholinergic (e.g., scopolamine, atropine), parasympathomimetics (e.g., carbachol, bethanechol, nicotine, methacholine, pilocarpine, donepezil, edrophonium, physostigmine, pyridostigmine, neostigmine, tacrine, echothiophate, isoflurophate, cisapride, metoclopramide, sildenafil, etc.), antihypertensive agents (e.g., prazosin, propranolol, timolol, metoprolol, pindolol, labetalol, guanethidine, reserpine, methyldopa, guanabenz, clonidine, nifedipine, captopril, enalapril, lisinopril, verapamil, diltiazem, thiazides, furosemide, hydralazine, minoxidil, nitroprusside, etc.), antiangina drugs (e.g., nicardipine, nadolol, diltiazem, isosorbide mononitrate, isosorbide dinitrate, metoprolol, nitroglycerine, amlodipine, nifedipine, atenolol, etc.), narcotic analgesics (e.g., morphine, codeine, heroin, methadone, etc.), narcotic antagonists (e.g., naloxone, naltrexone, etc.), anti-asthma/bronchodilatorsors (e.g., albuterol/salbutamol, ephedrine, metaproterenol, terbutaline, epinephrine, theophylline, ipratropium, salmeterol, fluticasone, formoterol, beclomethasone, fluticasone, etc.), blood factors such as factor VII, VIII, and IX, etc., bone metabolism agents such as calcitriol (vitamine D3), alendronate, etc., prostaglandins (e.g., alprostadil, dinoprost, latanoprost, misoprostol, etc.), protease inhibitors such as aprotinine, etc., antiparkinsonian agents (e.g., levodopa, carbidopa, amantadine, selegiline, entacapone, biperiden, benserazide, apomorphine, etc.), various contrast and diagnostic agents, and combinations of such agents.

In some preferred embodiments, the biologically active agent is curcumin. Curcumin (CUR; diferuloyl methane) is the major yellow pigment extracted from turmeric root (*Curcuma longa*; family-Zingiberaceae), a spice used in Ayurvedic herbal remedies. CUR is a potential and promising active agent with a variety of pharmacological activities. Although CUR has a tremendous potential as a therapeutic agent, it possesses three drawbacks: (a) it rapidly degrades in physiological solutions via hydrolysis and autoxidation into pharmacologically inactive compounds, and it was shown that total degradation products of CUR and isolated bicyclopentadione, a major autoxidative product, dramatically reduced biological effects compared to the parent agent, such as decreased anti-proliferative activity and apoptosis in MC38 colon cancer cells, and significantly inhibited LPS-induced inflammatory responses and NF-kB signaling in macrophage cells. It has also been shown that when CUR degradation is suppressed (by redox active antioxidants), the biological activities of CUR are enhanced, implying that the oxidative degradation products cannot play as mediators of CUR effects. (b) due to its low water solubility, CUR is slightly absorbed into the body with a very low bioavailability, and (c) the portion absorbed in the body is rapidly metabolized and excreted ($t_{1/2}$=28.2 and 44.5 min after IV. and oral curcumin in rats, respectively). Due to its rapid metabolic transformation, it is hypothesized that the observed pharmacological effects are not caused by CUR itself but are due to its metabolites.

In some other preferred embodiments, the biologically active material is granisetron. Granisetron (GR), a selective 5-HT3 receptor antagonist, have been used therapeutically for the prevention of delayed nausea and vomiting associated with emetogenic cancer chemotherapy. The activity of granisetron lays in competitive binding to the 5-HT3 receptors present in the CNS, and in the GI tract also. GR is commercially available as an oral tablet (2 mg/day or 1 mg twice daily), an IV infusion (1-3 mg or 10-40 μg/Kg body weight), as well as a sustained release SC injection, and a transdermal patch (52 cm' patch size, 34.3 mg drug). Drug plasma levels are usually low (ng/ml), especially after the oral dose, since granisetron is extensively metabolized in the liver. The average $C_{max}$ (1 mg oral dose) is 3.63 ng/ml, $t_{1/2}$ is 6.23 h, $V_d$ (volume of distribution) is 3.94 L/kg, protein binding is 65%, and the clearance (CL) is 0.41 L/h/Kg. The IV administration is inconvenient and painful at the injection site (even when using a short infusion), while patients taking GR tablets may suffer of variable bioavailability and non-compliance. The antiemetic efficacy is not unequivocally correlated with plasma concentrations of GR, which may imply on variable CNS availability. The subcutaneous GR and the transdermal patch have provided better alternatives, such as more predictable plasma concentrations with reduced toxicities that results from rapid elevation of plasma levels. The most frequent adverse effects of systemic granisetron is gastrointestinal disturbances, e.g. diarrhea or constipation, and QT-interval prolongation, which may be avoided by direct targeting the drug into the brain while reducing the dosage and circumventing the GI tract and the systemic blood circulation.

In some other preferred embodiments, the biologically active agent is a cannabinoid, e.g. cannabidiol. Cannabidiol (CBD), a natural, non-psychoactive, non-intoxicating substance obtained from industrial hemp (*Cannabis sativa*). Its biological activities include suppression of several cytokine production, thus making it a putative immunomodulatory therapeutic. In addition to its anti-inflammatory activity, CBD exhibits a broad spectrum of potential therapeutic properties in neurological disorders such as psychosis, epilepsy, anxiety, chronic pain, sleep, multiple sclerosis, fibromyalgia, as well as Alzheimer's, Parkinson's and Huntington's diseases. CBD also suppresses the growth of cancer cells and promote the death of these cells. However, the oral bioavailability of CBD in oil, the common mode of administration, is only about 6% in humans, much less than the 20-30% typically needed for a drug to achieve consistent therapeutic effects. This is due to its poor water solubility as well as poor absorption by its inability to transit the intestinal mucosa. Thus, although the lipophilic nature of CBD enables it to traverse the BBB, oral administration most often lack efficiency, does not allow reaching therapeutic dose in the brain region.

In some other preferred embodiments, the biologically active agent is insulin. It has been suggested that cerebral insulin may have therapeutic benefit for patients with Alzheimer's disease, i.e. facilitating cognition by increasing brain insulin signaling. In addition, cerebral insulin may be beneficial in control of food intake and body weight. Obese, hyper-insulinemic Zucker rats exhibit a reduction in the number of BBB insulin receptors, which may account for the decrease in CSF insulin uptake in obesity.

The delivery system for the biologically active materials, as described above, may contain the nanoparticles comprising the crosslinked polysaccharide, e.g. starch crosslinked with divanillin.

The delivery system may further comprise a diluent. The diluent may be selected from the list of polymers consisting of native starch, cationized guar gum, cellulose derivative, acrylic polymer, polysaccharide, mono- or di-saccharide, oligosaccharide, or protein. The delivery system as described above may further comprise poly- or oligo-hydroxy compounds selected from the list consisting of poly-alkylene glycols, polyglyceryl of fatty acids (e.g., Plurol oleique), poloxamers, and di- or tri-ethylene glycol ethyl ethers, alcohols, and sorbitol. When the delivery system is a nanoparticles' suspension, the preferred diluent is sorbitol.

In some embodiments the concentration of the diluent in said delivery system is between about 0.01% and about 80%.

The delivery system as described above may further comprise a plasticizer. The plasticizer may be selected from glycerol, propylene glycol, polyoxyethylene, polyoxypropylene, poloxamers, sorbitol, dextran, mannitol, alcohols, di- or tri-ethylene glycol ethyl ethers, and polyglyceryl of fatty acids. The preferred plasticizers include glycerol or propylene glycol. In some embodiments the concentration of the plasticizer in said delivery system is between about 0.01% and about 20%. Sometimes, when the delivery system is a nanoparticles' dispersion, particularly if manufactured from a microemulsion template as described below, the constituents of the microemulsion may act as the plasticizer for the polymer.

The delivery system as described above may further comprise a surfactant, said surfactant is selected from the list consisting of bile salt, lecithin, lysolecithin, phospholipids such as phosphatidylcholine, oleic acid and its derivatives thereof, fusidic acid and its derivatives thereof, polyoxyethylene alcohol ether, polyoxyethylene sorbitan derivatives such as the various Tweens, sorbitan ester of fatty acids such as sorbitan sesquioleate, sorbitan isostearate, sorbitan monolaurate, sorbitan monostearate, and sorbitan monooleate, sugar ester such as Sisterna sucrose esters, which are based on sucrose and vegetable fatty acids, capryloylcaproyl macrogol-8-glycerides (Labrasol), gelatine, albumin, polyvinylpyrrolidone, polyvinyl alcohol, cetostearyl alcohol, glyceryl monoesters of fatty acids (e.g., glyceryl monostearate, glyceryl monooleate, glyceryl dioleate, etc.), polyglyceryl-6-dioleate (Plurol oleique), polyoxyethyleneglycol derivatives of fatty acids (e.g., Myrj 45, 49, 51, 52, 52S, 53, 59 etc.), polyoxyethyleneglycol ethers (e.g., polyoxyethylene (23) dodecyl ether or Brij 35 etc.), and combination thereof. Each option represents a separate embodiment of the present invention. In some embodiments the concentration of the surfactant in said delivery system is between about 0.1% and about 50%, preferably, between 1% and 35%.

The delivery system as described above may further comprise a co-solvent, said co-solvent is glycerol, propylene glycol, polyoxyethylene and polyoxypropylene, propylene carbonate, tetraglycol (glycofurol; tetrahydrofurfuryl alcohol polyethyleneglycol ether), poloxamer, di or tri-ethylene glycol, ethyl ether, silicone, and sorbitol. The delivery system may also comprise polymer solubilizing agents, e.g. the materials that assist the polymer to subsist in an aqueous solution or accelerate the kinetics of the polymer dissolution. One example of such agent is urea; sometimes a base may be used to assist in dissolution of the polymer, e.g. sodium hydroxide. In some embodiments the concentration of the co-solvent in said delivery system is between about 0.1% and about 50%, preferably, between 5% and 25%.

The delivery system as described above may further comprise a preservative. The preservative may be selected from parabens, phenoxyethanol, benzyl alcohol, and benzoic acid. In some embodiments the concentration of the preservative in said delivery system is between about 0.001% and about 1%.

The delivery system as described above may further comprise antioxidant, said antioxidant is selected from the list consisting of carnosine, carotenoids, lipoic acid, uric acid, urocanic acid, citric acid, lactic acid, glutathione, cysteine, thioredoxin, sulfoxamine compounds, selenium, ethylenediaminetetraacetic acid (EDTA) and its salts, ethylene glycol tetraacetic acid (EGTA), butylhydroxytoluene (BHT), butylhydroxyanisole (BHA), ubiquinone, ubiquinol and other quinines, vitamin C, ascorbyl derivatives, vitamin E, tocopherols and tocopherol derivatives, retinoids, flavonoids such as quercetin, vitamin A and its derivatives, each option in a separate embodiments of the present invention. In some embodiments the concentration of the antioxidant in said delivery system is between about 0.01 and about 10%.

The delivery system as described above may further comprise saline or buffer, said buffer is selected from the list consisting of acids and salts of the following acids: phosphoric, citric, boric, acetic, benzoic, gluconic, lactic, glyceric, aconitic, adipic, ascorbic, carbonic, glutaric, glutamic, malic, succinic, tartaric, ethylene diamine tetraacetic (EDTA), as well as the following bases: triethanolamine, tromethamine (TRIS), glycine, diethanolamine, ammonia. In some embodiments the concentration of the buffer in said delivery system is between about 1% and about 99%.

The delivery system, particularly when formulated as a dispersion of nanoparticles, may further comprise a lipid, and/or a surfactant, and/or a cosolvent. Particularly preferred constituents of the delivery system include surfactants, such as caprylocaproyl polyoxyl-8 glyceride, and polyoxyl-40 hydrogenated castor oil, cosolvents, such as propylene carbonate, tetraglycol, and N-methyl pyrrolidone, and lipids, such as glyceryl oleate and dioleate, isopropyl palmitate, cetyl and/or stearyl alcohol, glyceryl triacetate, carnauba wax, or cocoa butter.

In a further aspect, the present invention provides a method for the preparation of the compositions of the invention. The method comprises combining, at a suitable temperature, an aromatic dialdehyde as described above, and a polysaccharide, as also described above. The combined polysaccharide and the aromatic dialdehyde may be kept together for a prolonged time interval, e.g. at least 30 minutes, or for 1 hour, to produce the polysaccharide chemically crosslinked by an aromatic dialdehyde. It has been surprisingly found that even an insoluble form of the aromatic dialdehyde, e.g. a slurry in water, is capable of efficiently crosslinking a dissolved polysaccharide, e.g. a starch. The reaction usually takes place at elevated temperature, e.g. above 30° C., more preferably between 35° C. and 45° C., or at times at even higher temperatures, e.g. at between 75 and 90° C. Without being bound by a theory it is presumed that the dissolved aromatic dialdehydes molecules react with the dissolved polysaccharide, thereby shifting the equilibrium towards better dissolution of the aromatic dialdehyde. The process naturally takes more time as the kinetics is governed not only by the reaction itself, but by the dissolution of the dialdehyde.

The polysaccharide and the aromatic dialdehydes are together combined in a medium, e.g. an aqueous medium, or in a microemulsion comprising aqueous phase. The medium is usually capable of dissolving the polysaccharide, at least at certain conditions. For example, starch may not be soluble in pure water if not pre-gelatinized, but if a slurry of starch in water is heated to about 80° C., a solution may be eventually obtained. Therefore, the medium may be water. Starch may also homogeneously solubilized in urea or in strong base medium such as sodium hydroxide solution, or in urea-base combination. The aqueous medium may also be a hydro-organic mixture, i.e. water containing up to 20% of an organic solvent. The organic solvent suitable for the application herein include ethyl alcohol, tetraglycol, N-methyl pyrrolidone, and others. The medium may also comprise a dilute acid, which may act as a catalyst for the crosslinking reaction of the polysaccharide and the aromatic dialdehyde.

Generally, the composition may be manufactured by a variety of processes. For example, the composition may be manufactured by cross-linking the polysaccharide in an aqueous medium or in an emulsion, followed by evaporating the solvents from the solution or the emulsion. In this way, polymeric films may be obtained by a variety of techniques as known in the art, including solvent casting, e.g. with a casting knife or a slit-die apparatus, by wet extrusion of an optionally partially dried solution or emulsion mixture, or by melt-extruding the dried composition.

Additionally, the composition may be obtained using spray-drying techniques as known in the art. Generally, the process may include a step of spray-drying a solution or an emulsion comprising said polysaccharide and said aromatic dialdehyde. The spray-drying may be performed at suitable temperatures to ensure efficient solvent removal, and at a solution feeding rate and atomization pressures adjusted to obtain the particles of desired size.

The process may also be performed using the nanoprecipitation techniques as known in the art, particularly to obtain nano-sized particles. Generally, the process will then comprise a step of forming nano-sized particles comprising said polysaccharide and said aromatic dialdehyde by adding an anti-solvent. For example, an aqueous medium containing a polysaccharide may then be added at a controlled rate to an organic solution comprising the biologically active material and the aromatic dialdehyde. Alternatively, the aqueous medium may contain both the polysaccharide dissolved therein and the aromatic dialdehyde in dispersed or dissolved form. The organic phase is usually kept under vigorous mixing, and the aqueous phase is usually a diluted solution, to ensure nanoprecipitation.

The process may also be performed using the salting out techniques as known in the art, particularly to obtain nano-sized particles. The process may then comprise a step of separating nano-sized particles comprising said polysaccharide and said aromatic dialdehyde by adding a salt. Generally, addition of a salt causes precipitation of solutes that have a poorer solubility than the salt. Therefore, nanoparticles of polysaccharides chemically crosslinked by an aromatic dialdehyde may be prepared (and separated) by adding a concentrated salt solution.

Additionally, the process may also be performed using the emulsion template techniques. The process may then comprise a step of providing a microemulsion or a nanoemulsion comprising said polysaccharide and/or said aromatic dialdehyde. The polysaccharide and the aromatic dialdehyde may be provided into a microemulsion precursor, e.g. a mixture of lipids and surfactants, and optionally cosolvents. The cross-linking of the polysaccharide may then occur inside the microemulsion droplets, thereby forming the nano-sized particles.

The nanoparticles may also be obtained in a non-cross-linked form, particularly the lipid-polymer nanoparticles. In this case, the nanoparticles themselves may be subjected to crosslinking with an aromatic dialdehyde. In this variant the process may comprise combining non-crosslinked lipid-polymer nanoparticles with an aromatic dialdehyde. The combined nanoparticles with the aromatic dialdehyde may be kept together for a desired time interval, e.g. for 1 hour, that may be required to effect crosslinking of the polysaccharide.

The nanoparticles obtained by any of these methods may be separated and purified from the solutions/emulsions wherein they are formed, by a variety of processes. One process is centrifugation at high g-force values, e.g. above 3000, for predetermined time intervals. The nanoparticles may then be collected from the pellet, and redispersed in a suitable medium. The nanoparticles may also be purified by a low g-force centrifugation, e.g. between 300 and 700-g, e.g. to remove large aggregates or unreacted materials, in which case the nanoparticles may be collected in the supernatant. The nanoparticles may also be purified by ion-exchange chromatography, as known in the art.

The final nanoparticles may be lyophilized in presence of a suitable diluent, e.g. mannitol, or may be diluted with a suitable medium and used as desired.

In an exemplary embodiment, the process may be carried out as follows. Maize starch is heated and mixed in purified water at about 80° C. until a homogenous slurry is formed. Alternatively, the polysaccharide, e.g. starch may be dissolved in a solution containing sodium hydroxide alone or in combination with urea. The aromatic dialdehyde (e.g., di-vanillin) is finely dispersed in water for example by using ultrasonic device, or alternatively, dissolved or partially dissolved in ethyl alcohol or N-methyl-2-pyrrolidone (Phar-masolve™). The dialdehyde dispersion or solution may then be then combined with the starch slurry at 80° C. and mixed, either in presence or in absence of an acid catalyst (acetic acid or diluted hydrochloric acid) and of a plasticizer. The mixture may then be allowed to remain under constant stirring for 1 hour at 80° C. Thereafter, to form a film, the mixture may be cast onto a Petri dish and left to dry at room temperature for overnight, or put in an heated, e.g. 100° C., ventilated oven, until a film is formed.

In a further aspect, the present invention provides a method for the preparation of the biodegradable nano-sized particles of the invention, comprising the polysaccharide crosslinked with an aromatic dialdehyde. The preferred polysaccharide is a starch. Other preferred polysaccharides include an alginic acid and salts thereof, and cellulose derivatives, e.g. hydroxypropyl cellulose.

In the description below, when curcumin is named as the active agent, it should be construed as exemplary active agent, which may be substituted for any other bioactive material, particularly for the preferred bioactive materials. Also, when divanillin is the named crosslinking aromatic dialdehyde, it may be used to denote any other aromatic dialdehyde, particularly the preferred aromatic dialdehydes. In some exemplary embodiments, nanoprecipitation method for starch NP manufacturing may be used. The formulation can be carried out by either way of the described below, by combining the aromatic dialdehyde with a dissolved poly-saccharide. An organic solution (e.g. in ethyl alcohol or in N-methyl pyrrolidone) of the active agent (e.g., curcumin), an aromatic di-aldehyde (e.g., di-vanillin) and an acid is transferred (e.g. via a syringe pump operated at a controlled rate) into either starch solution in sodium hydroxide/urea or a slurry in water, as described above. Alternatively, starch solution in sodium hydroxide/urea or a slurry in water as described above may be transferred using the syringe pump into an alcoholic solution of the active agent (e.g., curcumin), an aromatic di-aldehyde (e.g., di-vanillin) and an acid. Starch nanoparticles are thus precipitated by solvent exchange. Further alternatively, it may also be possible and preferable to combine an aromatic dialdehyde dispersion in water, with the aqueous mixture or solution of starch, and the resultant mixture may be then combined with an organic solution of the active agent and optionally acid. In presence of alcohol the crosslinked starch precipitates. The reaction mixture may then be thoroughly centrifuged, the supernatant is discarded, and the pellet then re-suspended in saline. When desired, particularly when larger particles are formed, the mixture may be purified by lightly centrifuging the mixture (e.g. at 500 g for 5 min) and discarding the pellet that contains large particles, e.g. unreacted divanillin excess and/or unreacted polysaccharide, then the alcohol is evaporated. Alternatively, the large particles may be removed by filtration through 0.45-micron membrane filter.

In some further embodiments, the nanoparticles may be prepared by microemulsion template method, as described below, by combining an aromatic dialdehyde with a polysaccharide solution inside a microemulsion. For example, polymer solution (e.g., starch, hydroxypropyl cellulose, etc.) or starch slurry is prepared, and added to a pre-prepared surfactant mixture (S-mix) to get a clear microemulsion. The surfactant mix may comprise a lipid and/or a surfactant and/or a cosolvent. The lipid and/or a surfactant and/or a cosolvent may be selected from the group consisting of caprylocaproyl polyoxyl-8 glyceride, polyoxyl-40 hydrogenated castor oil, propylene carbonate, tetraglycol, glyceryl oleate and dioleate, isopropyl palmitate, and cocoa butter. Preferably, the surfactant premix comprises cocoa butter, glyceryl oleate/dioleate mixture, tetraglycol, and polyoxyl-40 hydrogenated castor oil. Separately, microemulsion containing divanillin in the same S-mix components is also prepared. Both microemulsions are combined, the active agent, e.g. curcumin, granisetron, cannabidiol, or insulin, and optionally an acid are added and incubated at ambience or elevated temperature, e.g. between about 35° C. and about 45° C., for 0.5-1 hour. The formed nanoparticles can be isolated by phase separation and may be followed by ion-exchange chromatography. Alternatively, aromatic dialdehyde may be finely dispersed in water and added to an S-mix to get a clear microemulsion. In parallel, polymer solution (e.g., starch, hydroxypropyl cellulose, sodium alginate) or slurry in water is prepared and added to the microemulsion containing divanillin. Thereafter the active compound and optionally an acid are added, the microemulsion (ME) is allowed to stay at room temperature or at 40-50° C. for 1 h. The ME can be centrifuged, and the pellet is then re-dispersed to get NPs, or leave it as is. In either method, the aromatic dialdehyde, in this case divanillin, is not necessarily present in molecularly dissolved state inside the aqueous phase of the microemulsion, however, crosslinked polysaccharide (starch) is thus formed in either case.

Additionally, the present invention provides a method for the preparation of the biodegradable particles or capsules of the invention. Briefly, a microemulsion premix may be prepared by dissolving the surfactants, cosolvents and lipids, preferably at elevated temperatures. The microemulsion premix may then be combined with an aromatic dialdehyde aqueous dispersion and the drug, and finally with a polysaccharide solution. The resultant microemulsion may be left stirring at elevated temperatures for between 30 minutes and 2 hours, e.g. for 1 hour. The resultant solution contains the lipid nanoparticles, e.g. in form of nanocapsules. Alternatively, the dialdehyde may be added to the formed non-crosslinked nanocapsules, and left stirring at elevated temperatures, e.g. between about 35° C. and about 45° C., for a time interval between 0.5 and 3 hours.

As demonstrated in the appended examples below, the nano-sized particles according to the invention facilitate penetration of the biologically active materials into the brain, following intranasal administration. Therefore, as a further aspect, provided herein is a method of treatment of a subject in need thereof, by administering to the subject an amount of nano-sized capsules comprising a therapeutically effective amount of biologically active agents, i.e. the nano-sized capsules may be for use in the treatment of diseases responsive to the biologically active agents. The administering is preferably by intranasal route, i.e. inside the nose. The administration may be performed by a conventional spray, or a dropper. For the intranasal route, the biologically active agent is usually selected such that it exerts its activity inside the brain. The brain to plasma ratio is usually higher than obtainable from an intravenous or subcutaneous administration of the same biologically active material. The amount found in the brain of a test non-human mammal is usually at least 150% higher than that obtained by other routes of administration, i.e. conventional routes. It has been unexpectedly found that even insulin may be successfully delivered into the brain of a test non-human mammal, by intranasal administration of the nano-sized particles according to the invention, particularly by lipid-polymer nanoparticles. To reach the equivalent concentrations in the brain by conventional delivery would require such a dose of insulin as to cause a very significant to morbid hypoglycemia. The diseases or disorders amenable to said treatment, i.e. responsive to the increased intracerebral concentrations of certain biologically active materials, include psychosis, epilepsy, anxiety, chronic pain, migraine, insomnia, multiple sclerosis, fibromyalgia, Alzheimer's, Parkinson's and Huntington's diseases, ischemic stroke, and cancer.

A further possible route of administrations may be through the skin by a topical application of the nano-sized capsules, oral administration, subcutaneous reservoir, sublingual application, or intravenous administration.

EXAMPLES

Example 1—Polymeric Sheets

Formulation 1.1

| Ingredient | (g) |
| --- | --- |
| Maize starch | 1.5 |
| Di-vanillin | 0.3 |
| Ethanol | 4 ml |
| Glycerol | 0.18 |
| Water | 50 ml |

Glycerol was weighed in a chemical beaker, followed the water, and mixed with a magnetic mixer. Native maize starch (Hopkin&Williams Ltd, Chadwell Heath, Essex, England) was slowly added and dissolved using magnetic mixer for 30 minutes at 80° C. Separately, divanillin was dispersed in ethanol in a vial and added into the resultant solution. The mixture was left stirring for 30 minutes.

The resultant mixture was cast onto a square Petri dish, such that the amount cast was 0.6-1 ml/cm$^2$. The dish was left open and the solvent was evaporated overnight at ambience. The resultant films were tested as obtained or cured at 150° C. for 5 minutes.

The obtained film was separated from the substrate and cut into shapes suitable for the testing.

Thickness measurement was performed using Mitutoyo thickness gauge at 3 points per film. The average thickness obtained was about 200 μm.

Formulations 1.2-1.12

| | Formulation ID: | | | | | |
|---|---|---|---|---|---|---|
| Ingredient: | 1 .2 | 1.3 | 1.4 | 1.5.1 | 1.5 | 1.6 |
| Maize starch | 1.5 g | 1.5 g | 1.5 g 1.5 g | 1.5 g | 1.5 g |
| Di-vanillin | 0.3 g | 0.3 g | 0.3 g 0.3 g | 0.3 g | 0.2 g |
| Ethanol | 4 ml | 4 ml | 4 ml 60 ml | 4 ml | 4 ml |
| Glycerol | 0.36 g | 0.54 g | 0.72 g 0.77 g | 0.75 g | 0.75 g |
| Water | 50 ml | 50 ml | 50 ml 50 ml | 50 ml | 50 ml |
| Amount (g) cast per 1 cm$^2$ | 37.7 | 36.0 | 42.2 66.7 | 42.2 | 39.2 |

| | Formulation ID: | | | | | |
|---|---|---|---|---|---|---|
| Ingredient: | 1.7 | 1.8 | 1.9 | 1.10 | 1.11 | 1.12 |
| Maize starch | 1.5 g | 1.5 g | 0.9 g | 0.9 g | 0.9 g | 0.9 g |
| Di-vanillin | 0.1 g | 0.05 g | 0.18 g | 0.135 g | 0.09 g | 0.045 g |
| Ethanol | 4 ml | 4 ml | 6 ml | 6 ml | 6 ml | 6 ml |
| Glycerol | 0.75 g | 0.75 g | 0.45 g | 0.45 g | 0.45 g | 0.45 g |
| Water | 50 ml | 50 ml | 30 ml | 30 ml | 30 ml | 30 ml |
| Amount (g) cast per 1 cm$^2$ | 34.9 | 42.8 | | | | |

Similarly, the formulations 1.2-1.12 were prepared. Films, similar to 1.1 were obtained.

Example 2—Microemulsions-Assisted Crosslinking

Formulation 2.1

| | Formulation ID: | | | | |
|---|---|---|---|---|---|
| Ingredient: | 2.1 | 2.2 | 2.3 | 2.4 | 2.5 |
| Maize starch | 0.9 g | 0.9 g | 0.9 g | 0.9 g | 0.9 g |
| Di-vanillin (DV) | 0.135 g | 0.135 g | 0.135 g | 0.135 g | 0.135 g |
| Surfactant mixture (S-mix) | 3.17 | 0.45 | 0.90 | 0.90 | — |
| Propylene carbonate | | | | | 0.45 g |
| Ethanol | — | — | — | 4 ml | 4 ml |
| Water | 30 ml | 30 ml | 30.8 ml | | 30 ml |

S-Mix contained 15.7% Cithrol-GMO 50LQ, 46.8% Labrasol, and 37.5% propylene carbonate Similarly, the formulations 2.1-2.5 were prepared. The S-mix was prepared separately, and the required amounts of divanillin were dissolved therein. The mixture was added to the starch solution, as in the example 1. The obtained film of cross-linked starch was similar to the obtained in the example 1.

Example 3—Further Formulations were Produced to Optimize the Cross-Linker and the Plasticization

| | Formulation ID: | | | | | | | | |
|---|---|---|---|---|---|---|---|---|---|
| Ingredient: | 3.1 | 3.2 | 3.3 | 3.4 | 3.5 | 3.6 | 3.7 | 3.8 | 3.9 |
| Maize starch | 0.9 g | 0.9 g | 0.9 g | 0.9 g | 0.9 g | 0.9 g | 0.9 g | 0.9 g | 0.9 g |
| Di-vanillin | 0.135 g | 0.045 g | 0.09 g | 0.18 g | 0.135 g | 0.135 g | 0.135 g | 0.135 g | 0.135 g |
| Glycerol | 0.45 g | 0.45 g | 0.45 g | 0.45 g | | 0.3 g | 0.225 g | 0.15 g | 0.45 g |
| Tetraglycol | | | | | 0.45 g | | | | |
| Ethanol | 4 ml | 4 ml | 4 ml | 4 ml | 4 ml | 4 ml | 4 ml | 4 ml | 4 ml |
| Water | 30 ml | 30 ml | 30 ml | 30 ml | 30 ml | 30 ml | 30 ml | 30 ml | 30 ml |
| Film thickness, μm | 150-180 | 200 | 190 | 200 | 190-200* | 140-150 | 150-170 | 160-180* | 200 |

*the film was brittle

Tetraglycol is also known as glycofurol or tetrahydrofurfuryl alcohol polyethyleneglycol ether (CAS: 31692-85-0).

For the mechanical testing, the film was cut into 15×50 mm rectangular shape, and left equilibrating at 50% of relative humidity and 20-22° C. in for 24 hours prior to testing. The mechanical test was performed using LRX Plus Materials Test Machine (Lloyd Instruments Ltd., Fareham Hants, UK), with maximum 10N load cell, and 0.1 mm/s driving speed. The Young's modulus was determined by plotting extension stress (in MPa) versus percentage strain.

The following formulations were prepared for the comparison purposes, without effective cross-linker:

| Ingredient: | Formulation ID: | |
| --- | --- | --- |
| | 3A.1 | 3A.2 |
| Maize starch | 0.9 g | 0.9 g |
| Di-vanillin (DV) | — | — |
| Vanillin | — | 0.135 g |
| Glycerol | 0.45 g | 0.45 g |
| Ethanol | 4 ml | 4 ml |
| Water | 30 ml | 30 ml |

The results are presented in FIGS. 1-4. It can be seen that the maximum stress has somewhat increased with the increasing cross-linking ratio, and the elongation was significantly reduced. It can also be seen that after curing the films become more similar one to another. The films become more brittle, as evidenced by the decrease in the maximum strain (as elongation percentage).

Example 4—the Acid Catalysis

| Ingredient: | Formulation ID: | | |
| --- | --- | --- | --- |
| | 4.1 | 4.2 | 4.3 |
| Maize starch | 0.9 g | 0.9 g | 0.9 g |
| Di-vanillin (DV) | 0.135 g | 0.135 g | — |
| Vanillin | — | — | 0.135 g |
| 1N HCl | — | 0.1 g | 0.1 g |
| Glycerol | 0.45 g | 0.45 g | 0.45 g |
| Ethanol | 4 ml | 4 ml | 4 ml |
| Water | 30 ml | 30 ml | 30 ml |
| Film thickness, μm | 200 | 170-190 | 170-190 |

The films were prepared according to the general procedure of the example 1. The acid solution was added to water prior to addition of divanillin. Additionally, a film with vanillin, an aldehyde that does not possess cross-linking ability, was used.

The obtained films were similar to the obtained in the example 1. The film of the non-crosslinked formulation 4.3 (containing vanillin) was significantly weaker and dissolved rapidly in water.

Example 5—Acid-Catalyzed Polymeric Films

Additional formulations were prepared according to the general procedure of the example 1.

| Ingredient: | Formulation ID: | | | | | | |
| --- | --- | --- | --- | --- | --- | --- | --- |
| | 5.1 | 5.2 | 5.3 | 5.4 | 5.6 | 5.9 | 5.10 |
| Maize starch | 0.5 g | 0.5 g | 0.5 g | 1.0 g | 1.0 g | 1.0 g | 1.5 g |
| Di-vanillin (DV) | 0.075 g | 0.075 g | 0.025 g | 0.15 g | 0.05 g | 0.1 g | 0.075 g |
| Glycerol | 0.167 g | 0.167 g | 0.167 g | 0.334 g | 0.334 g | 0.334 g | 0.5 g |
| Ethanol | 2 ml | 2 ml | 2 ml | 3 ml | 3 ml | 3 ml | 4 ml |
| Hydrochloric acid | 0.05 ml (1N) | 0.1 ml (0.5N) | 0.1 ml (0.5N) | 0.1 ml (0.5N) | 0.1 ml (0.5N) | 0.1 ml (0.5N) | 0.1 ml (0.5N) |
| Water | 10 ml | 10 ml | 10 ml | 15 ml | 15 ml | 15 ml | 20 ml |
| Film thickness, μm | 350-400 | 260-300 | 250 | | | | 300-350 |

Further formulations included the following:

| Ingredient: | Formulation ID: | | | | | | | | | |
| --- | --- | --- | --- | --- | --- | --- | --- | --- | --- | --- |
| | 5.11 | 5.12 | 5.13 | 5.14 | 5.15 | 5.17 | 5.18 | 5.19 | 5.20 | 5.21 |
| Maize starch | 1.5 g | 2.0 g | 2.0 g | 2.0 g | 1.0 g | 1.0 g | 1.0 g | 1.0 g | 1.0 g | 1.0 g |
| Di-vanillin (DV) | 0.15 g | 0.04 g | 0.1 g | 0.2 g | 0.02 g | 0.1 g | 0.15 g | 0.2 g | 0.1 g | 0.1 g |
| Glycerol | 0.5 g | 0.67 g | 0.67 g | 0.67 g | 0.33 g | 0.33 g | 0.33 g | 0.33 g | 0.5 g | 1.0 g |
| Ethanol | 4 ml | 4 ml | 4 ml | 4 ml | 4 ml | 4 ml | 4 ml | 4 ml | 4 ml | 4 ml |
| Hydrochloric acid 0.5N | 0.1 ml | 0.2 ml | 0.2 ml | 0.2 ml | 0.1 ml | 0.1 ml | 0.1 ml | 0.1 ml | 0.1 ml | 0.1 ml |
| Water | 20 ml | 50 ml | 50 ml | 50 ml | 30 ml | 30 ml | 30 ml | 30 ml | 30 ml | 30 ml |
| Film thickness, μm | | | | | 200 | 200 | 170-180 | 200-250 | 200-250 | 300 |

The obtained films were of similar quality to the films obtained in the example 1.

The films 5.4 and 5.6 were subjected to water containing dirt for 32 days to simulate environmental biodegradation. Degradation was observed in both films, however film 5.4 (15% crosslinking) was relatively more stable than 5% cross-linked film (film 5.6), whereas most of the film was degraded and eliminated.

Example 6—Preparation of Nanoparticles by Nanoprecipitation of the Polymer in Presence of the Active Agent Formulation #SNP-01

| Step | Ingredient | (g) | Comments |
|---|---|---|---|
| 1 | Ethyl alcohol (or acetone) | 10 ml | |
| 2 | Divanillin (DV) | 15 mg | DV was dissolved in (1) using an ultrasonic bath |
| 3 | Curcumin (CUR) | 50 mg | CUR was added into (2) |
| 4 | Starch aqueous solution 2% | 10.0 | Starch was added dropwise into (3) |
| 5 | Mixing 1-4 for overnight under the hood or evaporate by using a Rotavapor Buchi Ion Exchange Chromatography: | | |
| 6 | Purolite S930 (cation exchange resin) | 4.0 | |
| 7 | Ionization with 0.5N NaOH, washing with water following by Elution of Step (5) with 20-30 ml of water | | |
| 8 | Acidification with 0.5N HCl | pH ≈4 | As needed until color was changed |
| 9 | Mannitol | Qs ad 0.1% | |
| 10 | Freeze drying | | |

Divanillin was dissolved in ethyl alcohol, using an ultrasonic bath. To the resultant solution, curcumin was added and mixed until dissolution. Separately, a 2% solution of starch was prepared by dissolving 1 gram of starch in 50 mL of water. The requisite amount of starch solution was added into the curcumin/divanillin ethanolic solution, and the obtained mixture was evaporated overnight in a ventilated hood, until dryness.

The obtained mixture was purified using ion-exchange chromatographic column, loaded with Purolite S930 cation exchange resin, by eluting with about 30 mL of water. The resultant eluate was acidified with 0.5-N hydrochloric acid to pH of about 4, by color indicator. Mannitol was then added, to the amount of 0.1% weight by the obtained volume, and the resultant mixture was lyophilized till dryness.

A further formulation was prepared, SNP-02, described in the table below. The nanoparticles were prepared as for formulation SNP-01. The obtained crude nanoparticle mixture was redispersed in water and filtered through 0.45 μm filter membrane. The filtrate was provided with mannitol and lyophilized.

Formulation #SNP-02

| Step | Ingredient | (g) | Comments |
|---|---|---|---|
| 1 | Ethyl alcohol (or acetone) | 10 ml | |
| 2 | Divanillin (DV) | 15 mg | DV was dissolved in (1) using an ultrasonic bath |
| 3 | Curcumin (CUR) | 50 mg | CUR was added into (2) |
| 4 | Starch aqueous solution 2% | 10.0 | Starch was added dropwise into (3) |
| 5 | Mixing 1-4 for overnight under the hood or evaporate by using a Rotavapor Buchi | | |
| 6 | Filtering through 0.45 μm nylon membrane and collect the filtrate | | |
| 7 | Mannitol | | As required to reach 0.1% |
| 8 | Freeze drying | | |

Formulation #SNP/C-01

| Step | Ingredient | (g) | |
|------|-----------|-----|---|
| 1 | Starch | 0.5 | |
| 2 | Urea | 1.0 | |
| 3 | Sodium hydroxide | 0.8 | |
| 4 | Purified water | 50 | ml |
| [A] | Stir until complete dissolution | | |
| 5 | Divanillin (DV) | 75 | mg |
| 6 | Purified water | 2 | ml |
| [B] | Sonicate for 480s | | |
| | Mix [A] + [B] and fill a syringe | | |
| 7 | Curcumin (CUR) | 5 | mg |
| 8 | Ethyl alcohol | 20 | ml |
| 9 | Acetic acid (98%) | 0.05 | ml |
| [C] | Mix for 5 minutes until CUR is dissolved | | |

The solutions were prepared according to the table above along the lines of the examples above. The mixture of divanillin and starch solution were introduced into the curcumin solution using a syringe pump operated at a controlled rate of 9 ml/min, to transfer the syringe contents, under continuous stirring. Upon completion of the addition, the mixture was centrifuged at 4600-g for 15 minutes, and the supernatant was discarded. The nanoparticle pellet was re-suspended in normal saline and was kept sealed at 4-8° C.

Formulation #SNP/C-02

| Step | Ingredient | (g) | |
|------|-----------|-----|---|
| 1 | Starch aqueous solution (2% w/v) | 10 | |
| 2 | 0.5N HCl solution | 0.05 | |
| [A] | Mix | | |
| 3 | Divanillin (DV) | 15 | mg |
| 4 | Curcumin (CUR) | 5 | mg |
| 5 | Ethyl alcohol | 10 | ml |
| [B] | Stir until complete dissolution | | |

The solutions were prepared according to the table above along the lines described above for the previous examples. The aqueous solution of starch in acid was added dropwise into the organic solution of divanillin and curcumin, at a rate of 0.05 ml/min at RT under continuous stirring. The organic solvent was evaporated in a rotor evaporator, and the resultant the nanoparticle suspension was filtered through 0.45 μm membrane filter (Nylon) to collect the filtrate. To the filtrate mannitol was added to the final concentration 0.1% w/v, and the solution was lyophilized.

Formulation #SNP/Blank1

| Step | Ingredient | (g) | |
|------|-----------|-----|---|
| 1 | Starch aqueous solution (2% w/v) in NaOH/urea 0.8:1 (as in C-01) | 1 | ml |
| [A] | | | |
| 2 | Curcumin (CUR) | 5 | mg |
| 3 | Ethyl alcohol | 20 | ml |
| [B] | Stir until complete dissolution | | |

The nanoparticles were prepared as for SNP/C01, without the crosslinking agent. The obtained average NP size was 167 nm with a wide distribution.

Formulation #SNP/Blank2

| Step | Ingredient | (g) |
|------|-----------|-----|
| 1 | Starch | 0.01 |
| 2 | Urea | 0.02 |

-continued

| Step | Ingredient | (g) | |
|------|-----------|-----|---|
| 3 | Sodium hydroxide | 0.016 | |
| 4 | Purified water | 0.95 | |
| 5 | Tween 80 | 0.04 | |
| [A] | Vortex until complete dissolution | | |
| 6 | Curcumin (CUR) | 5 | mg |
| 7 | Ethyl alcohol | 20 | ml |
| [B] | Stir until complete dissolution | | |

Similarly, formulations SNP/Blank2 and Blank3 were prepared.

Formulation #SNP/Blank3

| Step | Ingredient | (g) | |
|------|-----------|-----|---|
| 1 | Starch aqueous solution (3% w/v) | 0.03 | |
| 2 | Urea | 0.02 | |
| 3 | Sodium hydroxide | 0.016 | |
| 4 | Purified water | 0.95 | |
| [A] | Stir until complete dissolution | | |
| 5 | Curcumin (CUR) | 5 | mg |
| 6 | Ethyl alcohol | 20 | ml |
| 7 | Acetic acid | 0.05 | ml |
| [B] | Stir until complete dissolution | | |

Further formulations of cross-linked starch nanoparticles was prepared:

Formulation #SNP/C-03

| Step | Ingredient | (g) | |
|------|-----------|-----|---|
| 1 | Starch | 0.01 | |
| 2 | Urea | 0.01 | |
| 3 | Sodium hydroxide | 0.008 | |
| 4 | Purified water | 1 | ml |
| [A] | Stir until complete dissolution | | |
| 5 | Divanillin (DV) | 2 | mg |
| 6 | N-methyl-2-pyrrolidone (Pharmasolve ™) | 0.1 | ml |
| [B] | Vortex | | |
| | Mix [A] + [B] and fill a syringe | | |
| 7 | Curcumin (CUR) | 5 | mg |
| 8 | Ethyl alcohol | 20 | ml |
| 9 | Acetic acid (98%) | 0.1 | ml |
| [C] | Mix for 5 minutes until CUR is dissolved | | |

Formulation #SNP/C-04

| Step | Ingredient | (g) | |
|------|-----------|-----|---|
| 1 | Starch | 0.02 | |
| 2 | Urea | 0.01 | |
| 3 | Sodium hydroxide | 0.008 | |
| 4 | Purified water | 1 | ml |
| [A] | Stir until complete dissolution | | |
| 5 | Divanillin (DV) | 15 | mg |
| 6 | N-methyl-2-pyrrolidone (Pharmasolve ™) | 0.1 | ml |
| [B] | Vortex | | |
| | Mix [A] + [B] and fill a syringe | | |
| 7 | Curcumin (CUR) | 5 | mg |
| 8 | Ethyl alcohol | 20 | ml |
| 9 | Acetic acid (98%) | 0.2 | ml |
| [C] | Mix for 5 minutes until CUR is dissolved | | |

The solutions were prepared according to the table above along the lines of the examples above. The mixture of divanillin solution in NMP and starch solution were introduced into the curcumin solution using a syringe pump operated at a controlled rate of 0.05 ml/min, to transfer the syringe contents, under continuous stirring. Upon completion of the addition, the mixture was centrifuged at 4600-g for 15 minutes, and the supernatant was discarded. The nanoparticle pellet was re-suspended in normal saline and was kept sealed at 4-8° C. Average NP size was 73 nm with narrow distribution (for SNP/C-03), and 64 nm with narrow distribution (for SNP/C-04).

A further formulation was prepared:

Formulation #SNP/C-05

| Step | Ingredient | (g) |
|---|---|---|
| 1 | Aqueous starch solution (2%) [without NaOH/urea] | 10.0 |
| 2 | Acetic acid (98%) | 0.05 ml |
| [A] | Stir for 5 min at 35-40° C. | |
| 3 | Divanillin (DV) | 15 mg or 60 mg |
| 4 | N-methyl-2-pyrrolidone (Pharmasolve ™) | 0.1 ml |
| [B] | Vortex | |
| 5 | Curcumin (CUR) | 5 mg |
| 6 | Ethyl alcohol | 20 ml |
| [C] | Mix for 5 minutes until CUR is dissolved | |

Formulation #SNP/Blank4

| Step | Ingredient | (g) |
|---|---|---|
| 1 | Aqueous starch solution (2%) [without NaOH/urea] | 10.0 |
| 2 | Acetic acid (98%) | 0.05 ml |
| [A] | Stir for 5 min at 35-40° C. | |
| 3 | Curcumin (CUR) | 5 mg |
| 4 | Ethyl alcohol | 20 ml |
| [C] | Mix for 5 minutes until CUR is dissolved | |

The solutions were prepared according to the tables above along the lines of the examples herein. The organic solutions were introduced into the starch solution using a syringe pump operated at a controlled rate of 0.05 ml/min, to transfer the syringe contents, under continuous stirring and heating to ca. 35-40° C. Upon completion of the addition, the mixture was centrifuged at 500-g for 5 minutes, and the pellet was discarded. The supernatant was evaporated to dryness, the resultant particles were re-suspended in normal saline and kept sealed at 4-8° C. Average NP size was 144 nm with narrow distribution (for SNP/C-05), and 143 nm with narrow distribution (for SNP/Blank4).

Some of the obtained nanoparticles were tested in-vivo as described below.

Example 7—Starch-Based Nanoparticles Production Using Microemulsion Template

In these formulation, the surfactant mixture S-mixB was used, was prepared as follows:

| Ingredient | (g) |
|---|---|
| Isopropyl palmitate | 4.50 |
| Labrasol ® (caprylocaproyl polyoxyl-8 glyceride) | 19.70 |
| CITHROL-GMO 50-LQ(AP) (Croda) [glycery oleate and dioleate] | 6.56 |
| Propylene carbonate | 5.25 |

Formulation #CNP/S-01

| Step | Ingredient | (g) |
|---|---|---|
| 1 | Microemulsion precursor (S-mixB) for starch | 4.5 |
| 2 | Microemulsion precursor (S-mixB) for divanillin | 4.5 |
| 3 | Starch aqueous solution 1% | 0.5 |
| 4 | Curcumin (CUR) | 0.05 |
| 5 | Divanillin (DV) | 0.75 mg |
| 6 | Purified water | 0.5 ml |
| 7 | Mixing 1-6 for 30 minutes Phase separation: | |
| 8 | NaCl 6% solution Ion Exchange Chromatography: | 10 ml |
| 9 | Purolite A380 (anion exchange resin) | 4.0 |
| 10 | Elution with 0.1N NaOH and | 54 ml |
| 11 | Acidification with 0.5N HCl | 0.8 ml |
| 12 | Mannitol | 0.055 |
| 13 | Freeze drying | |

Starch aqueous solution was prepared as described above. The aliquot according to the table was mixed with the amount of S-mixB, whereto curcumin was added and mixed until dissolution. Divanillin was dissolved in the denoted amount of S-mixB, followed by purified water. The both components were combined and mixed together for 30 minutes. Thereafter, sodium chloride solution was added to separate the nanoparticles.

The nanoparticles were purified using Purolite A380 anion exchange resin with elution with sodium hydroxide solution. The eluate was acidified, mannitol was added to the solution, and it was then lyophilized.

Similarly, formulation CNP/S-02 and blank nanoparticles were prepared, according to the tables below.

Similarly, the formulation CNP/S-03 was prepared according to the table further below. Divanillin and curcumin were dissolved in the microemulsion precursor, and aqueous starch solution was added therein in dropwise manner. The mixture was left overnight at 4° C., then the nanoparticles were separated with sodium chloride solution, purified by ion-exchange chromatography, and lyophilized with mannitol.

Formulation #CNP/S-02

| Step | Ingredient | (g) |
|---|---|---|
| 1 | Microemulsion precursor (S-mixB) for starch | 4.5 |
| 2 | Microemulsion precursor (S-mixB) for divanillin | 4.5 |
| 3 | Starch aqueous solution 1% | 0.5 |
| 4 | Curcumin (CUR) | 0.05 |
| 5 | Divanillin (DV) | 0.75 mg |
| 6 | 0.4 ml Purified water + 0.1 ml 0.5N HCl | 0.5 ml |
| 7 | Mixing 1-6 for 30 minutes Phase separation: | |
| 8 | NaCl 6% solution Ion Exchange Chromatography: | 10 ml |
| 9 | Purolite A380 (anion exchange resin) | 4.0 |
| 10 | Elution with 0.1N NaOH and | 65 ml |
| 11 | Acidification with 0.5N HCl | 1.1 ml |
| 12 | Mannitol | 0.066 |
| 13 | Freeze drying | |

Formulation #CNP/S-B1 (Empty NPs)

| Step | Ingredient | (g) |
|------|-----------|-----|
| 1 | Microemulsion precursor (S-mixB) for starch | 4.5 |
| 2 | Microemulsion precursor (S-mixB) for divanillin | 4.5 |
| 3 | Starch aqueous solution 1% | 0.5 |
| 4 | Curcumin (CUR) | — |
| 5 | Divanillin (DV) | 0.75 mg |
| 6 | 0.4 ml Purified water + 0.1 ml 0.5N HCl | 0.5 ml |
| 7 | Mixing 1-6 for 30 minutes | |
| | Phase separation: | |
| 8 | NaCl 6% solution | 10 ml |
| | Ion Exchange Chromatography: | |
| 9 | Purolite A380 (anion exchange resin) | 4.0 |
| 10 | Elution with 0.1N NaOH and | 64 ml |
| 11 | Acidification with 0.5N HCl | 1.1 ml |
| 12 | Mannitol | 0.069 |
| 13 | Freeze drying | |

Formulation #CNP/S-03

| Step | Ingredient | (g) |
|------|-----------|-----|
| 1 | Microemulsion precursor (S-mixB) | 8.0 |
| 2 | Divanillin (DV) | 3 mg |
| 3 | Curcumin (CUR) | 0.05 |
| 4 | Starch aqueous solution 2% | 2.0 |
| 5 | Mixing 1-4 for 5 minutes and leave for overnight for 4° C. | |
| 6 | Phase separation: NaCl 6% solution | 20 ml |
| 7 | Ion Exchange Chromatography: Purolite A380 | 4.0 |
| 8 | Elution with 0.1N NaOH and | 187 ml |
| 9 | Acidification with 0.5N HCl | pH≈4 |
| 10 | Mannitol | 0.187 |
| 11 | Freeze drying | |

Example 8—Lipid Polymer Nanoparticles

Surfactant-mixture (S-mixC) was used for the microemulsion precursor in the formulations below.

| Ingredient | (g) |
|-----------|-----|
| Kolliphore RH-40 [polyoxyl-40 hydrogenated castor oil] | 33.34 |
| Tetraglycol | 30.00 |
| CITHROL-GMO 50-LQ(AP) (Croda) [glycery oleate and dioleate] | 16.66 |
| Cocoa butter | 20.00 |

The ingredients were heated to 50° C. and mixed until a homogeneous liquid was obtained. Thereafter, the mixture was cooled to ambience and used as needed.

The following formulations were prepared:

Formulation #SNP/LP-01

| Step | Ingredient | (g) | Comments |
|------|-----------|-----|----------|
| 1 | Starch | 0.1 | |
| 2 | 1N NaOH | 1.0 ml | |
| 3 | Purified water | 4.0 ml | |
| [A] | Dissolve while mixing at 80° C. | | |
| 4 | Divanillin (DV) | 1.2 mg | |
| 5 | Purified water | 30 ml | |
| [B] | Sonicate for 5 min | | |
| 6 | S-mixC | 2.0 | |
| 7 | X-linker dispersion [B] | 0.75 ml | 0.05% x-linker on polymer basis |
| | Mixing at 80° C. and cooling to 50° C. | | |
| 8 | Curcumin (CUR) | 2 mg | |
| | Stir until CUR is dissolved | | |
| 9 | Polymer solution [A] | 3.0 | 60 mg polymer |
| | Mix at 50° C. for 1-2 min until a clear O/W ME obtained | | 35% oil-in-water ME |
| 10 | Acetic acid (98%) | 0.06 ml | |

Starch was dissolved in water at 80° C. in presence of sodium hydroxide solution. Separately, divanillin was dispersed thoroughly in water, and an aliquot according to the table was mixed with S-mixC, heated to 80° C., and mixed until dissolution, after cooling to 50° C. Thereto curcumin was added and mixed until dissolution, followed by an aliquot according to the table, of the starch solution, followed by acetic acid. Nanoparticles were obtained.

Similarly, formulations SNP/LS-01, SNP/LS-02 and SNP/LS-03 were prepared.

Formulation #SNP/LS-01

| Step | Ingredient | (g) | Comments |
|---|---|---|---|
| 1 | Corn starch | 0.1 | |
| 2 | Purified water | 5.0 ml | |
| [A] | Mixing at 80° C. until the liquid turns clear, then cooling to RT | | |
| 3 | Divanillin (DV) | 1.2 mg | |
| 4 | Purified water | 7.5 ml | |
| [B] | Sonicate for 5-6 min | | |
| 5 | S-mixC | 2.35 | |
| 6 | X-linker dispersion [B], 2% x-linker on polymer basis | 0.25 ml | |
| 7 | Curcumin (CUR) | 24 mg | |
| 8 | Polymer solution [A] | 1.0 | 20 mg polymer |
| 9 | Acetic acid (98%) | 0.025 ml | |
| | Mix the ME and incubate for 1 h at 40° C. under stirring | | 35% water-in-oil ME |
| 10 | Purified water (warmed to 40° C.) | 2.65 ml or 3.65 ml | Dilution to 62.5% or 67.7% aqueous phase |

Formulation #SNP/LS-02

| Step | Ingredient | (g) | Comments |
|---|---|---|---|
| 1 | Corn starch | 0.1 | |
| 2 | Purified water | 5.0 ml | |
| [A] | Mixing at 80° C. until the liquid turns clear, then cooling to RT | | |
| 3 | Divanillin (DV) | 1.2 mg | |
| 4 | Purified water | 7.5 ml | |
| [B] | Sonicate for 5-6 min | | |
| 5 | S-mixC | 2.35 | |
| 6 | X-linker dispersion [B] 2% x-linker on polymer basis | 0.25 ml | |
| 7 | Curcumin (CUR) | 24 mg | |
| 8 | Polymer solution [A] | 1.0 | 20 mg polymer |
| 9 | Acetic acid (98%) | 0.025 ml | |
| | Mix the ME and incubate for 1 h at 40° C. under stirring | | 35% water-in-oil ME |
| 10 | Dilution to 44.4% water: Purified water (warmed to 40° C.) | 0.6 ml | |

Formulation #SNP/LS-03

| Step | Ingredient | (g) | Comments |
|---|---|---|---|
| 1 | Corn starch | 0.05 | |
| 2 | Purified water | 5.0 ml | |
| [A] | Mixing at 80° C. until the liquid turns clear, then cooling to RT | | |
| 3 | Divanillin (DV) | 1.2 mg | |
| 4 | Purified water | 7.5 ml | |
| [B] | Sonicate for 5-6 min | | |
| 5 | S-mixC | 2.35 | |
| 6 | X-linker dispersion [B] 2% x-linker on polymer basis | 0.125 ml | |
| 7 | Purified water | 0.125 ml | |
| 8 | Curcumin (CUR) | 24 mg | |
| 9 | Polymer solution [A] | 1.0 | 10 mg polymer |
| 10 | Acetic acid (98%) | 0.025 ml | |
| | Mix the ME and incubate for 1 h at 40° C. under stirring | | 35% water-in-oil ME |
| 11 | Dilution to 44.4% water: Purified water (warmed to 40° C.) | 0.6 ml | |

Surfactant-mixture (S-mixC1) for the microemulsion precursor was used for the formulation SNP/LS-04 below, containing one quarter concentration of cocoa butter. S-mixC1 was manufactured as S-mixC.

| Step | Ingredient | (g) |
|---|---|---|
| 1 | Kolliphore RH-40 [polyoxyl-40 hydrogenated castor oil] | 1.98 |
| 2 | Tetraglycol | 3.58 |

-continued

| Step | Ingredient | (g) |
|---|---|---|
| 3 | CITHROL-GMO 50-LQ(AP) (Croda) [glycery oleate and dioleate] | 3.96 |
| 4 | Cocoa butter | 0.50 |

Formulation #SNP/LS-04

| Step | Ingredient | (g) | Comments |
|---|---|---|---|
| 1 | Corn starch | 0.05 | |
| 2 | Purified water | 5.0 ml | |
| [A] | Mixing at 80° C. until the liquid turns clear, then cooling to RT | | |
| 3 | Divanillin (DV) | 1.2 mg | |
| 4 | Purified water | 7.5 ml | |
| [B] | Sonicate for 5-6 min | | |
| 5 | S-mixC1 | 2.35 | |
| 6 | X-linker dispersion [B] | 0.125 ml | 2% x-linker on polymer basis |
| 7 | Purified water | 0.125 ml | |
| 8 | Curcumin (CUR) | 24 mg | |
| 9 | Polymer solution [A] | 1.0 | 10 mg polymer |
| 9 | Acetic acid (98%) | 0.025 ml | |
| | Mix the ME and incubate for 1 h at 40° C. under stirring | | 35% water-in-oil ME |
| 10 | Purified water (warmed to 40° C.) | 0.6 ml | Dilution to 44.4% aqueous phase |

Surfactant-mixture (S-mixC2) for the microemulsion precursor (half concentration of cocoa butter) was used for some of the formulations below. S-mixC2 was manufactured as S-mixC.

| Step | Ingredient | (g) |
|---|---|---|
| 1 | Kolliphore RH-40 [polyoxyl-40 hydrogenated castor oil] | 3.75 |
| 2 | Tetraglycol | 3.37 |
| 3 | CITHROL-GMO 50-LQ(AP) (Croda) [glyceryl oleate and dioleate] | 1.88 |
| 4 | Cocoa butter | 1.00 |

Starch was dissolved in water at 80° C. Separately, divanillin was dispersed thoroughly in water, and an aliquot according to the table was mixed with S-mixC2 and mixed until dissolution. Thereto curcumin was added and mixed until dissolution, followed by an aliquot according to the table, of the starch solution, and by acetic acid. The obtained microemulsion with 35% water was incubated for 1 hour at 40° C., and then diluted to final concentration of 44.4% of water. Nanoparticles were obtained. Similarly, blank lipid nanoparticles and native polymer nanoparticles were prepared (SNP/LS-05, SNP/LS-06-Blank, and SNP/LS-07-Blank, respectively).

Formulation #SNP/LS-05

| Step | Ingredient | (g) | Comments |
|---|---|---|---|
| 1 | Corn starch | 0.1 | |
| 2 | Purified water | 5.0 ml | |
| [A] | Mixing at 80° C. until the liquid turns clear, then cooling to RT | | |
| 3 | Divanillin (DV) | 1.2 mg | |
| 4 | Purified water | 7.5 ml | |
| [B] | Sonicate for 5-6 min | | |
| 5 | S-mixC2 | 2.35 | |
| 6 | X-linker dispersion [B] | 0.25 ml | 2% x-linker on polymer basis |
| 7 | Curcumin (CUR) | 24 mg | |
| 8 | Polymer solution [A] | 1.0 | 20 mg polymer |
| 9 | Acetic acid (98%) | 0.025 ml | |
| | Mix the ME and incubate for 1 h at 40° C. under stirring | | 35% water-in-oil ME |
| 10 | Purified water (warmed to 40° C.) | 0.6 ml | Dilution to 44.4% aqueous phase |

Formulation #SNP/LS-06-Blank (Lipid Nanoparticles without Polymer)

| Step | Ingredient | (g) |
|---|---|---|
| 1 | S-mixC2 | 2.35 |
| 2 | Purified water | 1.25 ml |
| 3 | Curcumin (CUR) | 24 mg |
| 4 | Acetic acid (98%) | 0.025 ml |
| | Mix the ME and incubate for 1 h at 40° C. under stirring | |
| 5 | Purified water (warmed to 40° C.) | 0.6 ml |

Formulation #SNP/LS-07-Blank (Lipid-Non-Crosslinked Polymer Nanoparticles)

| Step | Ingredient | (g) |
|---|---|---|
| 1 | Corn starch | 0.1 |
| 2 | Purified water | 5.0 ml |
| [A] | Mixing at 80° C. until the liquid turns clear, then cooling to RT | |
| 3 | S-mixC2 | 2.35 |
| 6 | Purified water | 0.25 ml |
| 7 | Curcumin (CUR) | 24 mg |
| 8 | Polymer solution [A] (equivalent to 20 mg of starch) | 1.0 |

-continued

| Step | Ingredient | (g) |
|------|-----------|-----|
| 9 | Acetic acid (98%)<br>Mix the ME and incubate for 1 h at 40° C. under stirring | 0.025 ml |
| 10 | Purified water (warmed to 40° C.) | 0.6 ml |

Example 9—Further Polysaccharides as Starting Materials

A further surfactant-mixture (S-mixA) was used for the microemulsion precursor in some of the formulations below.

| Ingredient | (g) |
|-----------|-----|
| Kolliphore RH-40 [polyoxyl-40 hydrogenated castor oil] | 33.34 |
| Tetraglycol | 30.00 |
| CITHROL-GMO 50-LQ(AP) (Croda) [glyceryl oleate and dioleate] | 16.66 |
| Isopropyl palmitate | 20.00 |

PEGylated hydrogenated castor oil was mixed with tetraglycol at 60° C. and mixed till dissolution. Separately, isopropyl palmitate was mixed with glyceryl oleates, and then with the solution of tetraglycol and PEGylated hydrogenated castor oil, and mixed until a homogenous liquid was obtained.
Formulation #SNP/P-01

| Step | Ingredient | (g) |
|------|-----------|-----|
| 1 | S-mixA for polymer | 3.5 |
| 2 | S-mixA for divanillin | 3.5 |
| 3 | Hydroxypropyl cellulose (HPC) 10% aqueous solution | 1.5 |
| 4 | Divanillin (DV) [equivalent to 1-2% x-linker on polymer basis] | 1.5-4.5 mg |
| 5 | Purified water | 1.5 |
| 6 | Curcumin (CUR) | 3 mg |
| 7 | Acetic acid (98%) | 0.05 ml |
| 8 | Phase separation: Purified water | 10 ml |

Additionally, SNP/P-02 was prepared.
Formulation #SNP/P-02

| Step | Ingredient | (g) |
|------|-----------|-----|
| 1 | S-mixA for polymer | 3.5 |
| 2 | S-mixA for divanillin | 3.5 |
| 3 | Hydroxypropyl cellulose (HPC) 10% aqueous solution | 1.5 |
| 4 | Divanillin (DV) (equivalent to 1-2% x-linker on polymer basis) | 1.5-4.5 mg |
| 5 | Purified water | 1.5 |
| 6 | Curcumin (CUR) | 3 mg |
| 7 | Ethyl alcohol | 0.5 |
| 8 | Acetic acid (98%) | 0.05 ml |
| 9 | Phase separation: Purified water | 10 ml |

The aqueous solution of HPC was mixed with the aliquot of S-mixA according to the table above. Then, divanillin was dissolved in the aliquot of S-mixA, followed by water and acetic acid. The two solutions were combined and mixed together, and curcumin was then added thereto. The mixture was stirred continuously until a clear liquid was obtained. Thereafter, purified water was added to effect the phase separation; the lower phase containing the nanoparticles was collected and retained.

Surfactant-mixture S-mixC as described above was used as the microemulsion precursor in some of the formulations below.

Formulation SNP/CC-01 was prepared as follows. Sodium alginate solution was prepared in water, and an aliquot according to the table below was mixed with an amount of S-mixC, until a clear liquid was obtained. Then, curcumin, divanillin, and acetic acid were added consecutively to the obtained mixture. Thereafter, purified water was added to the resultant microemulsion, to form nanoparticles.
Formulation #SNP/CC-01

| Step | Ingredient | (g) |
|------|-----------|-----|
| 1 | Alginic acid sodium salt | 0.1 |
| 2 | Purified water | 5 ml |
| 3 | S-mixC | 2.0 |
| 4 | Polymer solution [A] | 3.0 |
| 5 | Curcumin (CUR) | 2 mg |
| 6 | Divanillin (DV) equivalent to 3% x-linker on polymer basis | 1.8 mg |
| 7 | Acetic acid (98%) | 0.2 ml |
| 8 | Purified water | 5 ml |

The nanoparticles were separated by centrifugation at 6250-g for 10 minutes, the supernatant was decanted, and the pellet was reconstituted with fresh saline. The encapsulation efficiency was measured as 7.4%.
Formulation #SNP/CC-02

| Step | Ingredient | (g) |
|------|-----------|-----|
| 1 | Alginic acid sodium salt | 0.1 |
| 2 | Purified water | 5 ml |
| 3 | S-mixC | 2.0 |
| 4 | Polymer solution [A] | 3.0 |
| 5 | Curcumin (CUR) | 2 mg |
| 6 | Acetic acid (98%) | 0.2 ml |
| 7 | Purified water | 5 ml |
| 8 | Divanillin (DV) equivalent to 3% x-linker on polymer basis | 1.8 mg |
| 9 | N-methyl pyrrolidone (Pharmasolve ™) | 0.2 ml |
| 10 | Acetic acid (98%) | 0.05 ml |

Formulation SNP/CC-02 was prepared along the lines of formulation CC-01, with the following exception. Divanillin was dissolved in NMP with acetic acid, and the primary nanoparticles were prepared without the cross-linker, i.e. following addition of water and mixing to homogeneity, the microemulsion was separated by centrifugation at 6250-g for 10 minutes, and the pellet was re-suspended in water, wherein the divanillin solution was added, and left stirring for 1 hour. The entrapment efficiency was measured as 57%.
Formulation #SNP/CC-03

| Step | Ingredient | (g) |
|------|-----------|-----|
| 1 | Alginic acid sodium salt | 0.1 |
| 2 | Purified water | 5 ml |
| 3 | S-mixC | 2.0 |
| 4 | Polymer solution [A] | 3.0 |
| 5 | Curcumin (CUR) | 2 mg |
| 6 | Acetic acid (98%) | 0.2 ml |
| 7 | Purified water | 5 ml |
| 8 | Divanillin (DV) equivalent to 0.1% x-linker on polymer basis | 1.2 mg |
| 9 | Purified water | 30 ml |
|  | Purified water | 1.5 mL |
|  | DV dispersion | 1.5 mL |

Similarly, an aliquot of sodium alginate solution was mixed with S-mixC, curcumin and acetic acid, followed by the purified water, until a homogenous liquid was obtained. The nanoparticles were separated by centrifugation as above. Separately, divanillin was dispersed (1.2 mg in 30 mL) in water. The nanoparticles' pellet was re-suspended in the mixture of 1.5 mL of the divanillin dispersion diluted with 1.5 mL of water, and left stirring for another hour at ambience. The entrapment efficiency was measured as 31.2%. Formulation SNP/CC-04 was manufactured similarly, except for the reconstitution of the pellet, that was performed in 3 mL of divanillin dispersion.

Formulation #SNP/CC-04

| Step | Ingredient | (g) |
|---|---|---|
| 1 | Alginic acid sodium salt | 0.1 |
| 2 | Purified water | 5 ml |
| 3 | S-mixA | 2.0 |
| 4 | Polymer solution [A] | 3.0 |
| 5 | Curcumin (CUR) | 2 mg |
| 6 | Acetic acid (98%) | 0.2 ml |
| 7 | Purified water | 5 ml |
| 8 | Divanillin (DV) equivalent to 0.2% x-linker on polymer basis | 1.2 mg |
| 9 | Purified water | 30 ml |
|  | Divanillin suspension | 3 ml |

Likewise, formulation CC-05 was manufactured according to the table below.

Formulation #SNP/CC-05

| Step | Ingredient | (g) |
|---|---|---|
| 1 | Alginic acid sodium salt | 0.1 |
| 2 | Purified water | 5 ml |
| [A] | Dissolve while mixing | |
| 3 | S-mixC | 2.0 |
| 4 | Polymer solution [A] | 1.0 |
|  | Mix at 70° C.-80° C. until clear ME is obtained | |
| 5 | Stearylamine | 0.01 |
|  | Add to the W/O ME until dissolved | |
| 6 | Purified water | 2 ml |
| 7 | Curcumin (CUR) | 2 mg |
| 8 | Acetic acid (98%) | 0.2 ml |
|  | Mix (6), (7), and (8) in the polymeric ME | |
| 9 | Purified water | 5 ml |
|  | Mix and centrifuge at 6250 g for 10 min, decant the SN | |
| 10 | Divamilin (DV) equivalent to 0.2% x-linker on polymer basis | 1.2 mg |
| 11 | Purified water | 30 ml |
|  | Sonicate dispersion (8) + (9) reconstitute the pellet with 1 ml of the sonicated dispersion + 1 ml water. Leave for 1 h at RT. | |

The formulations with hydroxypropyl cellulose ("LP-02", "LP-03", and "LP-04") as the polymer were prepared along the methods as described above, according to the amounts and steps enumerated in the tables below.

Formulation #NP/LP-02

| Step | Ingredient | (g) |
|---|---|---|
| 1 | Hydroxypropyl cellulose (Klucel LF) | 0.1 |
| 2 | Purified water | 5.0 ml |
| [A] | Dissolve while mixing at RT | |
| 3 | Divanillin (DV) | 1.2 mg |
| 4 | Purified water | 30 ml |

-continued

| Step | Ingredient | (g) |
|---|---|---|
| [B] | Sonicate for 5 min | |
| 5 | S-mixC | 3.0 or 4.7 |
| 6 | X-linker dispersion [B], equivalent to 0.05% x-linker on polymer basis | 0.5 ml |
| 7 | Curcumin (CUR) | 2 mg |
| 8 | Polymer solution [A] | 2.0 |
| 9 | Acetic acid (98%) | 0.05 ml |
|  | Mix the ME and incubate for 1 h at RT under stirring | |
| 10 | Purified water | 1-3 ml |

Briefly, hydroxypropyl cellulose was dissolved in water at room temperature, and divanillin was dispersed in a further amount of water using ultrasonic bath. An aliquot of the divanillin dispersion was added to pre-weighed amount of S-mixC, followed by curcumin, the aliquot of HPC solution, and acetic acid. The obtained 35% microemulsion of water in oil (or 45%, depending on the amount of S-mixC) was left stirring at ambience for 1 hour, to obtain the nanoparticles. The microemulsion was diluted with purified water to effect the inversion of the microemulsion.

Formulation #NP/LP-03

| Step | Ingredient | (g) |
|---|---|---|
| 1 | Hydroxypropyl cellulose (Klucel LF) | 0.1 |
| 2 | Purified water | 5.0 ml |
| [A] | Dissolve while mixing at RT | |
| 3 | Divanillin (DV) | 1.2 mg |
| 4 | Purified water | 30 ml |
| [B] | Sonicate for 5 min | |
| 5 | S-mixC | 1.5 |
| 6 | X-linker dispersion [B], equivalent to 0.05% x-linker on polymer basis | 0.25 ml |
| 7 | Curcumin (CUR) | 18.3 mg |
| 8 | Polymer solution [A] | 1.0 |
| 9 | Acetic acid (98%) | 0.025 ml |
|  | Mix the ME and incubate for 1 h at RT under stirring | |
| 10 | Dilution: Purified water | 2.8 ml |

Formulation #NP/LP-04

| Step | Ingredient | (g) |
|---|---|---|
| 1 | Hydroxypropyl cellulose (Klucel LF) | 0.1 |
| 2 | Purified water | 5.0 ml |
| [A] | Dissolve while mixing at RT | |
| 3 | Divanillin (DV) | 1.2 mg |
| 4 | Purified water | 30 ml |
| [B] | Sonicate for 5 min | |
| 5 | S-mixC | 2.35 |
| 6 | X-linker dispersion [B], equivalent to 0.05% x-linker on polymer basis | 0.25 ml |
| 7 | Curcumin (CUR) | 24 mg |
| 8 | Polymer solution [A] | 1.0 |
| 9 | Acetic acid (98%) | 0.025 ml |
|  | Mix the ME and incubate for 1 h at RT under stirring | |
| 10 | Dilution: Purified water | 3.65 ml |

Example 10—the Accumulation of Curcumin in Rat Brain Following Intranasal Administration of Nanoparticles of the Present Invention Intranasal Administration of CUR-Loaded Nanoparticles into the Brain All animal treatments were performed in accordance with protocols reviewed and approved by the Institutional & Use Committee, Ben-Gurion University of the Negev, which complies with the Israeli Law of Human Care and Use of Laboratory Animals. Sprague-Dawley rats (male, 250-350 g of body weight, Harlan, Jerusalem) were used in this study. All animals were housed in polycarbonate cages and maintained on a 12/12 h light/dark cycle under controlled conditions of temperature and humidity. The rats had free access to food and water. Animals were randomly administered via the nasal route (IN) or intravenously (IV) via the tail vein. In case of IN route, the volume used was 15 μL per nostril, whereas for the IV route (tail vein), the volume used was 0.2 ml. The animals were sedated with isoflurane vapor just before IN or IV administration. After usually 60 minutes from administration, the animals were deeply anesthetized with ketamine (80 mg/kg, i.p.) and xylazine (10 mg/kg, i.p.).

the precursor. The microemulsion consisted of polyoxyl 40 hydrogenated castor oil, cocoa butter (*Theobroma* oil), tetraglycol and glyceryl oleate as S-mixC2 above. Corn starch (4% w/v) was dispersed and gelatinized in 80° C. water, then cooled to 40° C. Under a constant stirring, divanillin, curcumin, and a gelatinized starch slurry were added into the microemulsion in a 40° C. water bath. The pH was adjusted to 4 by acetic acid, and the liquid was kept stirring for 1 h then the pH was raised to 5-6 with 1 N NaOH solution. After dilution with an appropriate amount of water, the final ALN dispersion contained 1.9 mg curcumin per ml.

The following formulations were prepared, with varying amount of divanillin:

Formulation #LS-14

| Step | Ingredient | (g) | | Comments |
|---|---|---|---|---|
| 1 | Corn starch | 0.2 | | |
| 2 | Purified water | 5.0 | ml | |
| [A] | Mixing at 80° C. until the liquid turns clear, then cooling to RT | | | |
| 3 | Divanillin (DV) | 12 | mg | |
| 4 | Purified water | 7.5 | ml | |
| [B] | Sonicate for 5-6 min | | | |
| 5 | S-mixC2 | 2.35 | | |
| 6 | X-linker dispersion [B] | 0 | | not cross-linked |
| | | 0.125 | ml | 1% x-linker on polymer basis |
| | | 0.25 | ml | 2% x-linker on polymer basis |
| | | 0.375 | ml | 3% x-linker on polymer basis |
| | | 0.75 | ml | 6% x-linker on polymer basis |
| 7 | Curcumin (CUR) | 24 | mg | |
| 8 | Polymer solution [A] | 0.5 | | 20 mg polymer |
| 9 | Acetic acid (98%) | 0.025 | ml | |
| | Mix the ME and incubate for 1 h at 40° C. under stirring | | | 35% water-in-oil ME |
| 10 | Purified water (warmed to 40° C.) | 0.75 | ml | |
| | 1N sodium hydroxide solution (warmed to 40° C.) | 0.35 | ml | |

Then, 0.5 mL of blood was taken from the right atrium and transcardial perfusion was carried out with PBS 1× to eliminate residual blood from each organ, until the heart stopped. Brain was then removed, placed and washed with PBS, frozen at −80° C., and lyophilized until it was completely dry (~12 h). Finally, the tissue was ground and extracted with 2 ml methanol, centrifuged and the supernatant was taken into 1.5-ml amber vials and kept at −80° C. until analyzed by HPLC.

Formulations SNP/Blank4, SNP/C-05 7.5% x-linking (15 mg divanillin), and SNP/C-05 30% x-linking (60 mg divanillin) of the Example 6 were administered to the aminals as described above. The results are presented at FIG. 5. Further, formulation of Example 8, LP-04 was administered as described above. The results are shown in the following table:

| Time of application, h | Curcumin accumulation, μg |
|---|---|
| 0.5 | 0.052 |
| 1 | 0.324 |
| 1.5 | 0.130 |

Example 10a—Further Curcumin Nanoparticles Formulation and Brain Accumulation Following Intranasal Administration Curcumin-loaded nanoparticles (amylolipid nanovesicles—ALNs) were prepared by using a microemulsion as The particle size distribution for the formulations above was 132.3±43.9 for non-crosslinked particles, 147.8±62.2 for ALNs crosslinked with 2% of divanillin, 144.6±51.7 for ALNs crosslinked with 6% of divanillin, and 128.1±58.3 for polymer-free lipid nanoparticles.

For the in-vivo study, the animals were randomly divided into groups of at least three animals each. For the intranasal administration, the administered dose used in each animal was 160 μg curcumin/kg body weight, delivered within ca. $10^{12}$ nanoparticles/kg body weight. The applied volume was 86-87 μL/kg of body weight (30-34 μL; approx. ~15 μL/nostril). For the intravenous administration, hydroalcoholic solution for injection was prepared by dissolving 200 μg/ml of curcumin in a 3:7 ethanol-saline (sterile) solution. Aliquots of 280-320 μL from the solution were injected into the tail vein of a sedated animal (Dose=160 μg/kg body weight).

The animals were sedated with isoflurane vapor just before administration. After 60 min from administration, the animals were euthanized by $CO_2$ aspiration. Then, blood sample was taken by cardiopuncture into heparinized tubes. Blood in heparinized tubes was centrifuged at 10,000-g for 10 min and the separated plasma was transferred into vials and kept at −20° C. until analyzed by HPLC. The brain was then carefully excised, washed with saline, frozen at −80° C. and was lyophilized overnight.

Quantification of curcumin in plasma was performed by mixing 1-ml plasma sample with 2 ml of ethanol, followed by vortex stirring and centrifugation at 10,000 g for 10 min. Lyophilized brain was first ground by using a Teflon® pestle, then 2 ml of ethyl alcohol were added and mixed followed by centrifugation at 10,000-g for 10 min. The

| supernatant solutions of both plasma and brain extracts were analyzed immediately by HPLC.

Aliquots of 20 μL from each sample were injected into a HPLC system, equipped with a prepacked column (250×4.6 mm, 5 μm, Thermo Scientific™ Betasil C18). The HPLC system (Shimadzu VP series) consisted of an auto-injector and a diode array detector. The quantification of curcumin was carried out at 425 nm. The samples were chromatographed using an isocratic mobile phase consisting of acetonitrile-0.2% acetic acid solution (75:25) at a flow rate of 1 ml/min. A calibration curve (peak area versus drug concentration) was constructed by running standard drug solutions in ethanol for each series of chromatographed samples. Limit of quantitation was 0.01 μg/ml.

The results are summarized in the table below (and in FIG. 7), which demonstrates curcumin amounts found in plasma and brain 1 h after intranasal administration of nanoparticles to rats as compared to curcumin disposition 1 h following intravenous administration of hydroalcoholic solution; Curcumin dose=160 μg/kg.

|  | Brain, ng/g ± SD | plasma level, ng/mL ± SD | Brain/plasma ratio | n |
|---|---|---|---|---|
| IN-ALN | 141.46(±55.95) | 11.90(±12.06) | 7.06(±1.18) | 7 |
| IN-unmodified ALN | 18.21(±28.17) | 4.25(±6.81) | 5.10(±1.29) | 3 |
| IN-lipid NPs | 17.20(±14.47) | 7.35(±9.62) | 1.85(±0.00) | 3 |
| IV solution | 0 | 7.25(±0.20) | 0 | 2 |

In the table above: IN-ALN: Intranasal administration of amylolipid nanovesicles containing curcumin; IN-unmodified ALN: Intranasal administration of amylolipid nanovesicles made of non-crosslinked starch; IN-lipid NPs: Intranasal administration of solid nanoparticles made as ALNs without involving starch; IV solution: Intravenous administration of hydroalcoholic solution of curcumin.

It can be readily seen that the properties of the nanoparticles can be easily optimized using the cross-linking degree, and thus adapting the elasticity of the particles, especially in an aqueous medium, to provide an optimized delivery of the drug to the brain.

Example 11—In-Vitro Skin Penetration Study

The permeability of curcumin through animal skin was determined in vitro with a Franz diffusion cell system (Permegear, Inc., Bethlehem, PA). The diffusion area was 1.767 cm² (15 mm diameter orifice), and the receptor compartment volumes was from 12 ml. The solutions in the water-jacketed cells were thermostated at 37° C. and stirred by externally driven, Teflon-coated magnetic bars. Each set of experiments was performed with at least four diffusion cells (n≥4), each containing skin from a different animal. All animal procedures were performed in accordance with protocols reviewed and approved by the Institutional & Use Committee, Ben Gurion University of the Negev, which complies with the Israeli Law of Human Care and Use of Laboratory Animals. Sprague-Dawley rats (males, 350-400 g, Envigo RMS, Jerusalem, Israel) were euthanized by aspiration of $CO_2$. The abdominal hair was carefully clipped and sections of full-thickness skin were excised from the fresh carcasses of animals and used immediately. All skin sections were measured for transepidermal water loss (TEWL) before mounted in the diffusion cells or stored at lower temperatures until used. TEWL examinations were performed on skin pieces using Dermalab® Cortex Technology instrument, (Hadsund, Denmark) and only those pieces that the TEWL levels were less than 15 g/m²/h were introduced for testing. The skin was placed on the receiver chambers with the stratum corneum facing upwards, and the donor chambers were then clamped in place. The excess skin was trimmed off, and the receiver chamber, defined as the side facing the dermis, was filled with phosphate buffer (pH 7.4) containing α-tocopherol (0.01%). After 15 min of skin washing at 37° C., the buffer was removed from the cells and the receiver chambers were refilled with fresh phosphate buffer solution. 0.2 ml Aliquots of a nanoparticle suspension or a hydro-alcoholic solution were applied on the skin at time=0. Samples were withdrawn from the receiver solution at predetermined time periods. After the 6-h experimental period, each curcumin-exposed skin tissue was washed carefully in distilled water, wiped and tape-stripped (×10) to remove the residues of curcumin adsorbed over the stratum corneum. The tissue was then cut to small pieces and inserted into 20-ml vials. The skin pieces in each vial were extracted by 2-ml methanol. The extraction was completed after shaking the vial (750 rpm) overnight at 4° C. The receiver samples and the skin extracts were taken into 20-ml vials and kept at −80° C. until analyzed by HPLC.

One ml of each preparation was applied onto rat skin at CUR concentration of 0.5 mg/ml, in the formulations described in the Example 6 SNP/Blank1 as non X-linked NPs, SNP/C-03 as 20% x-linking, and SNP/C-04 as 75% x-linking. Hydroalcoholic (50:50) solution of CUR [0.5 mg/ml] was used neat. Curcumin accumulation in the skin is shown in FIG. 6.

Further, formulations SNP/LS-06 blank, SNP/LS-07 blank, and SNP/LS-05 of Example 7 were applied onto skin as described above. The results are shown in FIG. 8.

Example 12—Granisetron Formulations and the Accumulation of Granisetron in Rat Brain Following Intranasal Administration of Nanoparticles of the Present Invention To demonstrate the versatility of the compositions and processes described in conjunction with the present invention, granisetron was incorporated into lipid nanocapsules with crosslinked starch shell, i.e. into lipid polymer nanoparticles, and the permeation thereof into the rat brain was evaluated as follows.

Granisetron formulations were prepared as follows:
Formulation #SNP/GS-03 (Granisetron-Containing Lipid-Polymer Nanoparticles)

| Step | Ingredient | (g) |
|---|---|---|
| 1 | Corn starch | 0.1 |
| 2 | Purified water | 5.0 ml |
| [A] | Mixing at 80° C. until the liquid turns clear, then cooling to RT | |
| 3 | Divanillin (DV) | 12 mg |
| 4 | Purified water | 7.5 ml |
| [B] | Sonicate for 5-6 min | |
| 5 | S-mixC2 | 2.35 |
| 6 | X-linker dispersion [B], equivalent to 2% x-linker on polymer basis | 0.25 ml |
| 7 | Granisetron (GR) | 6 mg |
| 8 | Polymer solution [A] | 1.0 |
| 9 | Acetic acid (98%) | 0.025 ml |
|  | Mix the ME and incubate for 1 h at 40° C. under stirring | |
| 10 | Purified water (warmed to 40° C.) | 0.6 ml |

Formulation #SNP/GB-01

| Step | Ingredient | (g) |
|---|---|---|
| 1 | Corn starch | 0.2 |
| 2 | Purified water | 5.0 ml |
| [A] | Mixing at 80° C. until the liquid turns clear, then cooling to RT | |
| 3 | Divanillin (DV) | 12 mg |
| 4 | Purified water | 7.5 ml |
| [B] | Sonicate for 5-6 min | |
| 5 | S-mixC2 | 2.35 |
| 6 | X-linker dispersion [B] 2% x-linker on polymer basis | 0.25 ml |
| 7 | Granisetron (GR) | 5 mg |
| 8 | Polymer solution [A] | 0.5 |
| 9 | Acetic acid (98%) | 0.025 ml |
| | Mix the 25% w/o ME and incubate for 1 h at 40° C. under stirring | |
| 10 | Purified water (warmed to 40° C.) | 0.695 ml |
| | 1N NaOH solution (warmed) to 44.4% o/w | 0.405 ml |

Particle size (DLS measurement, after ×1200 dilution): 170 nm (94% weight of peak)—as seen in the FIG. 11. Drug concentration for GS-03: 1.4 mg/ml or after ×3 dilution 14 µg/30 µl volume dose, for GB-01: 1.2 mg/ml, or after ×3 dilution 12 µg/30 µl.

The intranasal administered dose used in each animal was 32 µg GR/kg body weight. The applied volume was approximately 15 µL per nostril. For intravenous administration, aqueous solution of GR hydrochloride was prepared by dissolving the drug in a sterile saline solution. Approximately 0.3 ml of the solution were injected into the tail vein of a sedated animal (GR HCl dose=36 µg/kg body weight). The animals were sedated with isoflurane vapor just before administration. Sixty minutes after the administration, the animals were euthanized by $CO_2$ aspiration. Then, blood sample was taken by cardiopuncture into heparinized tubes. Blood in heparinized tubes was centrifuged at 10,000-g for 10 min and the separated plasma was transferred into vials and kept at −20° C. until analyzed by HPLC. The brain was then carefully excised, washed with saline and frozen at −80° C.

Quantification of GR in plasma was performed by mixing 1 ml of plasma sample with 2 ml of methanol, followed by vortex stirring and centrifugation at 10,000-g for 10 min. The brain was homogenized with 2 ml of methanol/0.5 N HCl solution (1:1) followed by centrifugation at 10,000-g for 10 min. The supernatant solutions of both plasma and brain extracts were analyzed immediately by HPLC. Aliquots of 20 µl from each sample were injected into a HPLC system, equipped with a prepacked CN column. The quantification of GR was carried out at 301 nm. The samples were chromatographed using an isocratic mobile phase consisting of acetonitrile-acetate buffer solution pH5 (45:55) at a flow rate of 1 ml/min.

The formulations were administered intranasally as described above. Granisetron concentrations are summarized in the table below, demonstrating the drug's distribution 1 hour after IN and IV administrations (Dose=32 µg/Kg).

| | Brain Level (ng/g) | Plasma level (ng/ml) | B/P ratio |
|---|---|---|---|
| IN nanoparticles (GS-03) | 981.2 (±8.9) | 1190.0 (±41.8) | 0.86 (±0.23) |
| IN nanoparticles (GB-01) | 550.2 (±19.7) | 22.2 (±13.6) | 31.3 (±16.7) |
| IV injection | 59.7 (±0.5) | Undetectable | — |

The specific formulations based on the present invention have shown to be well absorbed through the nasal route and be targeted the brain in a level that is higher compared to the plasma level one hour after administration. The administered dose to rats' nostrils was 12 µg, which was calculated as 32 µg/kg body weight. It was within the dosage range given clinically by iv infusion of 5 minutes (10-40 µg/kg body weight). After IV administration of 36 µg/Kg GR-HCl dose, the average rat brain level was 59.7 ng/g, whereas no drug was detected in the plasma, suggesting a very high rate of metabolism compared to human. This brain concentration and the fact that no drug was detected after 1 h, indicates that after IV injection very small portion of the dose (ca. 0.64%) reached the brain while most of the drug distributed in the body tissues and metabolized. In contrast, after IN administration of the nanoparticles of the present invention, a very high accumulation of GR was found in the brain (550.2 ng/g tissue; 7.8% of the dose, formulation GB-01) and the mean plasma level was 22.2 ng/ml, which implies the circumventing the hepatic metabolism. It is clear from these findings that after IN administration of this amylolipid nanoparticle formulation, the drug was partly distributed in the body from the nasal vasculature but also was targeted directly to the brain and reached a very high brain levels. This high accumulation of GR in the brain after IN administration of amylolipid NPs indicates that even a lowering of the dose to one tenth (e.g. 1-4 µg/Kg) could lead to therapeutically optimal brain concentrations with a very low systemic exposure.

Example 13—Cannabidiol Formulations and the Accumulation of Cannabidiol in Rat Brain Following Intranasal Administration of Nanoparticles of the Present Invention To demonstrate a further versatility of the lipid polymer nanoparticles, cannabidiol was incorporated.

In brief, starch solution and divanillin dispersions were prepared as described above, according to the amounts in the table. To the microemulsion premix S-mixC2, the measured aliquot of the divanillin dispersion was added, followed by cannabidiol, the aliquot of the polymer solution and acetic acid. The resulting microemulsion was stirred at 40° C. for 1 hour, whereafter it was diluted as denoted in the table to 44.4% of water o/w emulsion. Final drug concentration: 10 mg/ml, or after ×3 dilution: 100 µg/30 µl volume, which is the dose for administration to the rats.

The formulations were as follows:

Lot #SNP/CBD-01 (Cannabidiol-Containing AmyloLipid Nanoparticles)

| Step | Ingredient | (g) |
|---|---|---|
| 1 | Corn starch | 0.2 |
| 2 | Purified water | 5.0 ml |
| [A] | Mixing at 80° C. until the liquid turns clear, then cooling to RT | |
| 3 | Divanillin (DV) | 12 mg |
| 4 | Purified water | 7.5 ml |
| [B] | Sonicate for 5-6 min | |
| 5 | S-mixC2 | 2.35 |
| 6 | X-linker dispersion [B], equivalent to 2% x-linker on polymer basis | 0.25 ml |
| 7 | Cannabidiol | 43 mg |
| 8 | Polymer solution [A] | 0.5 |
| 9 | Acetic acid (98%) | 0.025 ml |
| | Mix the 25% w/o ME and incubate for 1 h at 40° C. under stirring | |

-continued

| Step | Ingredient | (g) |
|------|-----------|-----|
| 10 | Purified water (warmed to 40° C.) | 0.695 ml |
| | 1N NaOH solution (warmed) to 44.4% water o/w microemulsion | 0.405 ml |

The administered intranasal dose used in each animal was 220 µg CBD/kg body weight. The applied volume was approximately 15 µL/nostril. For the intravenous dose, a solution of CBD for injection was prepared by dissolving CBD in a small portion of ethanol, then mixed with a sterile saline solution (pH7.4) containing 1.5% Tween 80 and 0.1% ascorbic acid. The final concentration of ethanol was 5%. The volume of 0.1 ml of the solution (1 mg CBD/ml) were injected into the tail vein of a sedated animal. The animals were sedated with isoflurane vapor just before administration. After 60 minutes from administration, the animals were euthanized by $CO_2$ aspiration. Then, blood sample was taken by cardiopuncture into heparinized tubes. Blood in heparinized tubes was centrifuged at 10,000-g for 10 min and the separated plasma was transferred into vials and kept at −20° C. until analyzed by HPLC. The brain was then carefully excised, washed with saline, frozen at −80° C. and lyophilized.

Quantification of CBD in plasma was performed by mixing 1-ml plasma sample with 2 ml of methanol, followed by vortex stirring and centrifugation at 10,000-g for 10 min. The dried brain was ground and extracted by 2 ml of methanol followed by centrifugation at 10,000-g for 10 min. The supernatant solutions of both plasma and brain extracts were analyzed immediately by HPLC. Aliquots of 20 µl from each sample were injected into a HPLC system, equipped with a prepacked C18 column. The quantification of CBD was carried out at 220 nm. The samples were chromatographed using an isocratic mobile phase consisting of acetonitrile–0.1% acetic acid solution (75:25) at a flow rate of 1 ml/min.

The results are shown in the Table below. The brain concentration obtained 1 h after IN administration of CBD-containing nanoparticles was 15.6 ng/g while no detectable concentration was found after iv administration of the same dose. The plasma levels of CBD after IN delivery were also higher than after IV injection, implying (1) systemic absorption, and (2) circumventing liver metabolism.

Cannabidiol distribution 1 hour after IN and IV administrations (Dose=220 µg/Kg)

| | Brain Level (ng/g) | Plasma level (ng/ml) | B/P ratio |
|--|--------------------|----------------------|-----------|
| IN nanoparticles | 15.6 (±7.7) | 105.5 (±40.1) | 0.17 (±0.09) |
| IV injection | Undetectable | 71.2 (±13.6) | — |

Example 14—Insulin Formulations and the Accumulation of Insulin in Rat Brain Following Intranasal Administration of Nanoparticles of the Present Invention The following example demonstrates that lipid nanoparticles coated by di-vanillin cross-linked starch can effectively deliver insulin to the brain via the intranasal route.

Insulin formulation was prepared as follows. Starch solution was prepared as described above, at 80° C., and was cooled prior to further use. Insulin was added to the solution and mixed thoroughly. Separately, divanillin was dispersed in water, as described above, under sonication for 5 minutes, and an aliquot of the dispersion was dissolved in the pre-weighed amount of S-mixC2. An aliquot of insulin-starch mixture was added to the microemulsion, followed by acetic acid. The resultant mixture was mixed for 1 hour at 40° C., to produce the nanoparticles. Thereafter, pre-warmed sodium hydroxide solution was added, to neutralize the pH of the preparation. The resultant drug concentration was 0.3 mg/ml, or after dilution with saline—7.1 µg per 30 µl volume dose ready for administration to rats.

Lot #SNP/INS-01 (Insulin-Containing AmyloLipid Nanoparticles)

| Step | Ingredient | (g) |
|------|-----------|-----|
| 1 | Corn starch | 0.2 |
| 2 | Purified water | 5.0 ml |
| | Mixing at 80° C. until the liquid turns clear, then cooling to RT | |
| 3 | Human insulin 100 mg/ml solution | |
| [A] | Add 3 to the cooled starch slurry | |
| 4 | Divanillin (DV) | 12 mg |
| 5 | Purified water | 7.5 ml |
| [B] | Sonicate for 5-6 min | |
| 6 | S-mixC2 | 2.35 |
| 7 | X-linker dispersion [B], equivalent to 2% x-linker on polymer basis | 0.25 ml |
| 8 | Insulin-Starch slurry of step [A] | 0.51 |
| 9 | Acetic acid (98%) | 0.025 ml |
| | Mix the 25% w/o ME and incubate for 1 h at 40° C. under stirring | |
| 10 | 1N NaOH solution (warmed) | 0.2 ml |

Formulation INS-01 was used for intranasal administration. The administered dose used in each animal was 28 µg INS/kg body weight. The applied volume was approximately 15 µL/nostril. For intravenous (iv) and subcutaneous (sc) administrations, a solution of insulin for injection was prepared by dissolving human insulin in a sterile saline solution to obtain a concentration of 90 µg/ml. A volume of 0.1 ml of the solution (9 µg dose, i.e. 36 µg/kg) was injected into the tail vein of a sedated animal, or under the loose skin over the neck. The animals were sedated with isoflurane vapor just before administration. After 60 minutes from administration, the animals were euthanized by $CO_2$ aspiration. Then, blood sample was taken by cardiopuncture into heparinized tubes. Blood in heparinized tubes was centrifuged at 10,000 g for 10 min and the separated plasma was transferred into vials and kept at −20° C. until analyzed by ELISA. The brain was then carefully excised, washed with saline, and frozen at −80° C.

Quantification of insulin in plasma was performed by mixing 1-ml plasma sample with 1 ml of methanol, followed by vortex stirring and centrifugation at 10,000-g for 10 min. The brains were homogenized with 2 ml of water followed by centrifugation at 10,000-g for 10 min. The supernatant solutions of both plasma and brain extracts were analyzed by ELISA, by a Human INS ELISA Kit utilizing the sandwich principle (Wuhan Fine Biotech Co., Ltd. Wuhan, Hubei, China; Catalogue No. EH0374).

As shown in below, the brain concentration obtained 1 h after intranasal administration of insulin-containing nanoparticles was 2.56 ng/g, which was equivalent to the mean levels found after iv (1.87 ng/g) and sc (3.52 ng/g) administrations of similar doses. Unlike brain levels, the plasma levels of insulin after intranasal delivery were significantly lower than after iv and sc injections, indicating (a) no significant systemic exposure and (b) that insulin can bypass the BBB by the intranasal administration in nanoparticles according to the invention. This finding is very important since it designates that intranasal administration of insulin may be feasible also to non-diabetic patients, without the otherwise inevitable hypoglycemic side effects.

|  | Brain Level (ng/g) | Plasma level (ng/ml) | B/P ratio |
| --- | --- | --- | --- |
| IN nanoparticles (GB-01) | 2.56 (±0.80) | 0.29 (±0.20) | 8.67 |
| SC administration | 3.52(±0.40) | 2.65 (±0.16) | 1.33 |
| IV injection | 1.87(±1.08) | 4.56 (±1.60) | 0.41 |

Example 15—Crosslinking with Further Aromatic Dialdehydes

Besides di-vanillin, other naturally-originated di-alde-hyde can be used to modify starch and other polysaccharides for biodegradable compositions both in drug delivery and for film preparation: di-cinnamaldehyde, di-coniferylalde-hyde (also called di-ferulic aldehyde; coniferylaldehyde is a flavonoid isolated from cinnamon), di-coumaraldehyde and di-sinapaldehyde (sinapaldehyde is enzymatically formed from coniferylaldehyde).
Formula 250918

| Ingredient | (g) |
| --- | --- |
| Maize starch | 1.0 |
| Di-coniferylaldehyde (or di-ferulic aldehyde) | 0.165 ml solution |
| Glycerol | 0.33 |
| Ethanol | 165 microliter |
| Acetic acid | 0.05 ml |
| Water | 30 ml |

Formula 300918

| Ingredient | (g) |
| --- | --- |
| Maize starch | 1.0 |
| Di-cinnamaldehyde | 53 mg |
| Glycerol | 0.33 |
| Ethanol | 1 ml |
| Acetic acid | 0.05 ml |
| Water | 30 ml |

The solutions were prepared and films were cast as described above. Acceptable films were formed.

Example 16—Proof of Reaction of Dispersed Aromatic Dialdehyde Divanillin with Saccharides Procedure: 2 mg of divanillin (DV) were dispersed in 4 ml water by sonication for 480 sec. 24 mg of glucose were dissolved in the dispersion, and then acetic acid (50 ml) was added. The reaction mixture was placed in a 90° C. water bath for 1 h under stirring.

HPLC-UV analysis: 0.5 ml of the reaction mixture was diluted with 0.5 ml water, and aliquots of 20 ml were injected into a HPLC system (Shimadzu VP series), equipped with a prepack C18 column (5 mm, 250×4.6 mm). The sample was chromatographed using an isocratic mobile phase consisting of acetonitrile-0.1% acetic acid solution (70:30) at a flow rate of 1 ml/min. The detection was carried out at 234 nm.

MS analysis: Peak 3.6 was collected and was injected into a Sciex API 2000 triple-quadrupole mass spectrometer (MDX SCIEX, Concord, Ontario, Canada) equipped with a TurboIonSpray source and controlled by Analyst software. The unknown substance of peak 3.6 was detected by means of mass spectrometry using electron impact ionization in the positive mode. The instrument's settings were: declustering potential 130V, focusing potential 350V, Entrance potential 10V, ion spray potential 5500V, curtain gas 10 psi, ion source gas 25 psi. The following product ions (m/z) were detected: 1552, 1508, 1464, 1420, all by intervals of 44 Dalton. When scanning the analyte at lower molecular weights (m/z from 100 to 700), the same phenomenon was observed (see FIG. 12$b$). The 44-dalton fragments seem to be derived from a residue of carbons 5 and 6 of the glucose rings: $>$CH—CH$_2$—OH. The resulted hydrophilic polymer contains a huge number of glucose molecules, every 4 glucose moieties bound by two acetal groups to the biphenyl skeleton of the divanillin structure (see an example of the polymeric structure below). Since a polymer possesses a high molecular weight there are many possibilities for generating fragments losing 44 dalton residues from each glucose moiety.

The chromatogram is shown in the FIG. 12 $a$. A new peak at 3.6 min appears besides the two peaks at 4.8 min and 7 min of vanillin and divanillin, respectively. Mass-spectrum of the main peak is shown in the FIG. 12 $b$. Divanillin peak is reduced significantly, implying that it was more active as a precursor than vanillin. The suggested structure of the adduct is shown in the FIG. 12 $c$.

The invention claimed is:

1. A composition of matter comprising starch chemically crosslinked by divanillin, and a bioactive material, which is an antibody drug conjugate, or a peptide drug conjugate.

2. The composition of claim 1, in the form of a polymeric sheet, or a polymeric particle/capsule.

3. The composition of claim 1, which is a pharmaceuti-cally acceptable formulation.

4. The composition of claim 1, in the form of nano-sized particles.

5. The composition of claim 1, further comprising a lipid and/or a surfactant and/or a cosolvent.

6. The composition of claim 5, wherein the lipid and/or a surfactant and/or a cosolvent are selected from the group consisting of caprylocaproyl polyoxyl-8 glyceride, poly-oxyl-40 hydrogenated castor oil, propylene carbonate, tet-raglycol, glyceryl oleate and dioleate, isopropyl palmitate, and cocoa butter.

7. The composition of claim 6, wherein the lipid and/or a surfactant and/or a cosolvent comprises at least one member of the group consisting of polyoxyl-40 hydrogenated castor oil, tetraglycol, and glyceryl oleate.

8. The composition of claim 7, wherein the lipid and/or a surfactant and/or a cosolvent comprises polyoxyl-40 hydro-genated castor oil.

9. The composition of claim 7, wherein the lipid and/or a surfactant and/or a cosolvent comprises tetraglycol.

10. The composition of claim 7, wherein the lipid and/or a surfactant and/or a cosolvent comprises glyceryl oleate.

* * * * *